US010752900B2

(12) United States Patent
Tonelli et al.

(10) Patent No.: US 10,752,900 B2
(45) Date of Patent: Aug. 25, 2020

(54) OLIGONUCLEOTIDES FOR MODULATING GENE EXPRESSION AND USES THEREOF

(71) Applicant: BIOGENERA S.P.A., Porretta Terme (IT)

(72) Inventors: Roberto Tonelli, Granarolo Emilia (IT); Leonardo Venturelli, Calderara di Reno (IT); Andrea Tortori, Citerna (IT); Luca Montemurro, Bologna (IT)

(73) Assignee: BIOGENERA S.P.A., Porretta Terme (IT)

( * ) Notice: Subject to any disclaimer, the term of this patent is extended or adjusted under 35 U.S.C. 154(b) by 0 days.

(21) Appl. No.: 16/009,303

(22) Filed: Jun. 15, 2018

(65) Prior Publication Data

US 2018/0282731 A1 Oct. 4, 2018

Related U.S. Application Data

(62) Division of application No. 14/379,729, filed as application No. PCT/IB2013/051410 on Feb. 21, 2013, now Pat. No. 10,023,867.

(30) Foreign Application Priority Data

Feb. 24, 2012 (IT) .............................. MI2012A0275

(51) Int. Cl.

| | |
|---|---|
| ***A61K 48/00*** | (2006.01) |
| ***C07H 21/04*** | (2006.01) |
| ***C12N 15/113*** | (2010.01) |
| ***A61K 31/475*** | (2006.01) |
| ***A61K 31/555*** | (2006.01) |
| ***A61K 31/7048*** | (2006.01) |
| ***A61K 31/7105*** | (2006.01) |
| ***A61K 33/24*** | (2019.01) |

(52) U.S. Cl.

CPC ........ *C12N 15/1135* (2013.01); *A61K 31/475* (2013.01); *A61K 31/555* (2013.01); *A61K 31/7048* (2013.01); *A61K 31/7105* (2013.01); *A61K 33/24* (2013.01); *C12N 2310/11* (2013.01); *C12N 2310/14* (2013.01); *C12N 2310/3181* (2013.01); *C12N 2310/321* (2013.01); *C12N 2310/322* (2013.01); *C12N 2310/3231* (2013.01); *C12N 2310/3233* (2013.01); *C12N 2310/3513* (2013.01); *C12N 2320/31* (2013.01)

(58) Field of Classification Search

CPC ............................ A61K 31/713; C12N 15/113
See application file for complete search history.

(56) References Cited

U.S. PATENT DOCUMENTS

2008/0038783 A1 2/2008 Anderson
2011/0171184 A1 7/2011 Hovig et al.
2015/0159162 A1 6/2015 Collard et al.

FOREIGN PATENT DOCUMENTS

WO 2001061030 A2 8/2001
WO 2002092617 A1 11/2002
WO 2003070917 A2 8/2003
WO 2004096826 A2 11/2004
WO 2005045032 A2 5/2005
WO 2009009739 A2 1/2009

OTHER PUBLICATIONS

Bentwich, I., "Viral regulatory miRNA SEQ ID No. 234415" Dec. 28, 2007.

Bentwich, I., "Viral Regulatory miRNA SEQ ID No. 369957" Dec. 28, 2007.

Cao, et al., "Antisense Oligodeoxynucleotide Directed to NF-kB-RelA Down Regulates bcl-XL mRNA in Drug-Resistant Leukemia Cell Line HL-60/E6", Journal of Experimental Hematology, Issue 9, No. 4, pp. 294-296, Aug. 31, 2001.

Catapano, et al, "Inhibition of gene expression and cell proliferation by triple helix-forming oligonucleotides directed to c-myc gene," Biochemistry, 2000, 39 5126-5138.

Christensen et al., "Stopped-Flow Kinetics of Locked Nucleic Acid (LNA)-Oligonucleotide Duplex Formation: studies of LNA-DNA and DNA-DNA interactions." Biochem. J. 2001, 354, 481-484.

Communication relating to the results of the partial international search report of PCT/IB2013/051410, dated Jun. 28, 2013.

Cutrona, et al., "Effects in live cells of a c-myc anti-gene PNA linked to a nuclear localization signal," Nature Biotechnology vol. 18, Mar. 2000 300-303.

Faccini A., et al., "Circular dichroism study of DNA binding by a potential anticancer peptide nucleic acid targeted against the MYCN oncogene", Chirality, vol. 20:494-500, 2008.

International Search Report of PCT/IB2013/051410, dated Sep. 16, 2013.

Kim, et al, "Inhibition of Transcription of the human c-myc protooncogene by intermolecular triplex", Biochemistry 1998, 37, 2299-2304.

Naghama, et al., "Nuclease Resistant Methylphosphate-DNA/LNA chimeric oligonucleotide", Bioorganic & Medicinal Chemistry Letters, 19 (2009) 2707-2709.

Napoli, et al., "Growth inhibition and apoptosis induced by daunomycin-conjugated triplex-forming oligonucleotides targeting the c-myc gene in prostate cancer cells," Nucleic Acid Research, 2006, vol. 34, No. 2 734-744.

Office Action dated Jun. 28, 2016 in Counterpar Chinese Application No. 201380009360.1, Serial No. of Notification 201606231764380.

(Continued)

*Primary Examiner* — Amy H Bowman
(74) *Attorney, Agent, or Firm* — Silvia Salvadori, P.C.; Silvia Salvadori

(57) ABSTRACT

The present invention regards oligonucleotides for modulating the expression of a gene, in particular for modulating a gene responsible for a pathology of genetic, tumoural or viral origin.

Moreover, the present invention relates to the use of said oligonucleotides, possibly chemically modified, for the treatment and/or the diagnosis of said diseases.

15 Claims, No Drawings

Specification includes a Sequence Listing.

(56) References Cited

OTHER PUBLICATIONS

Office Action dated Mar. 2017 in connection with counterpart chinese patent application 201380009360.1.
Office Action dated Sep. 20, 2016 in counterpart Japanese application 2014-558247.
Rossi, J., "Transcriptional activation by Small RNA duplexes", Nature Chem Biology, vol. 3, No. 3, pp. 136-137 (2007).
Thomas, et al, "Suppression of c-myc oncogene expression by a polyamine-complexed triplex forming oligonucleotide in MCF-7 breast cancer cells," Nucleic Acid Research, 1995, vol. 13, No. 17 3594-3599.

SEQUENCE LISTING

<160> NUMBER OF SEQ ID NOS: 84

<210> SEQ ID NO 1
<211> LENGTH: 16

```
<212> TYPE: DNA
<213> ORGANISM: Artificial
<220> FEATURE:
<223> OTHER INFORMATION: ANTI MYCN PNA

<400> SEQUENCE: 1

atgccgggca tgatct                                                       16


<210> SEQ ID NO 2
<211> LENGTH: 16
<212> TYPE: DNA
<213> ORGANISM: Artificial
<220> FEATURE:
<223> OTHER INFORMATION: ANTI MYCN PNA

<400> SEQUENCE: 2

gggtggatgc gggggg                                                       16


<210> SEQ ID NO 3
<211> LENGTH: 16
<212> TYPE: DNA
<213> ORGANISM: Artificial
<220> FEATURE:
<223> OTHER INFORMATION: ANTI MYCN PNA

<400> SEQUENCE: 3

gatgcggggg gctcct                                                       16


<210> SEQ ID NO 4
<211> LENGTH: 16
<212> TYPE: DNA
<213> ORGANISM: Artificial
<220> FEATURE:
<223> OTHER INFORMATION: ANTI MYCN PNA

<400> SEQUENCE: 4

gtcggcggga ggtaag                                                       16


<210> SEQ ID NO 5
<211> LENGTH: 16
<212> TYPE: DNA
<213> ORGANISM: Artificial
<220> FEATURE:
<223> OTHER INFORMATION: ANTI MYCN PNA

<400> SEQUENCE: 5

gctgggtgga tgcggg                                                       16


<210> SEQ ID NO 6
<211> LENGTH: 16
<212> TYPE: DNA
<213> ORGANISM: Artificial
<220> FEATURE:
<223> OTHER INFORMATION: ANTI MYCN PNA

<400> SEQUENCE: 6

tggacgcgct gggtgg                                                       16


<210> SEQ ID NO 7
<211> LENGTH: 16
<212> TYPE: DNA
<213> ORGANISM: Artificial
<220> FEATURE:
<223> OTHER INFORMATION: ANTI MYCN PNA

<400> SEQUENCE: 7
```

-continued cgcgctgggt ggatgc 16

<210> SEQ ID NO 8
<211> LENGTH: 16
<212> TYPE: DNA
<213> ORGANISM: Artificial
<220> FEATURE:
<223> OTHER INFORMATION: ANTI MYCN PNA

<400> SEQUENCE: 8
gtctggacgc gctggg 16

<210> SEQ ID NO 9
<211> LENGTH: 16
<212> TYPE: DNA
<213> ORGANISM: Artificial
<220> FEATURE:
<223> OTHER INFORMATION: ANTI MYCN PNA

<400> SEQUENCE: 9
ccctgcagtc ggcggg 16

<210> SEQ ID NO 10
<211> LENGTH: 16
<212> TYPE: DNA
<213> ORGANISM: Artificial
<220> FEATURE:
<223> OTHER INFORMATION: ANTI MYCN PNA

<400> SEQUENCE: 10
cggccgcggg ccgcca 16

<210> SEQ ID NO 11
<211> LENGTH: 16
<212> TYPE: DNA
<213> ORGANISM: Artificial
<220> FEATURE:
<223> OTHER INFORMATION: ANTI MYCN PNA

<400> SEQUENCE: 11
gggaactgtg ttggag 16

<210> SEQ ID NO 12
<211> LENGTH: 16
<212> TYPE: DNA
<213> ORGANISM: Artificial
<220> FEATURE:
<223> OTHER INFORMATION: ANTI MYCN PNA

<400> SEQUENCE: 12
tgtctggacg cgctgg 16

<210> SEQ ID NO 13
<211> LENGTH: 16
<212> TYPE: DNA
<213> ORGANISM: Artificial
<220> FEATURE:
<223> OTHER INFORMATION: ANTI MYCN PNA

<400> SEQUENCE: 13
acgctcaggg accacg 16

<210> SEQ ID NO 14
<211> LENGTH: 16
<212> TYPE: DNA
<213> ORGANISM: Artificial

-continued

<220> FEATURE:
<223> OTHER INFORMATION: ANTI MYCN PNA

<400> SEQUENCE: 14
cccggacgaa gatgac 16

<210> SEQ ID NO 15
<211> LENGTH: 16
<212> TYPE: DNA
<213> ORGANISM: Artificial
<220> FEATURE:
<223> OTHER INFORMATION: ANTI MYCN PNA

<400> SEQUENCE: 15
actgtgttgg agccga 16

<210> SEQ ID NO 16
<211> LENGTH: 16
<212> TYPE: DNA
<213> ORGANISM: Artificial
<220> FEATURE:
<223> OTHER INFORMATION: ANTI MYCN PNA

<400> SEQUENCE: 16
cctgtcgtag acagct 16

<210> SEQ ID NO 17
<211> LENGTH: 16
<212> TYPE: DNA
<213> ORGANISM: Artificial
<220> FEATURE:
<223> OTHER INFORMATION: ANTI MYCN PNA

<400> SEQUENCE: 17
tgtgacagtc atctgt 16

<210> SEQ ID NO 18
<211> LENGTH: 16
<212> TYPE: DNA
<213> ORGANISM: Artificial
<220> FEATURE:
<223> OTHER INFORMATION: ANTI MYCN PNA

<400> SEQUENCE: 18
gtgacagtca tctgtc 16

<210> SEQ ID NO 19
<211> LENGTH: 16
<212> TYPE: DNA
<213> ORGANISM: Artificial
<220> FEATURE:
<223> OTHER INFORMATION: ANTI MYCN PNA

<400> SEQUENCE: 19
gacagtcatc tgtctg 16

<210> SEQ ID NO 20
<211> LENGTH: 16
<212> TYPE: DNA
<213> ORGANISM: Artificial
<220> FEATURE:
<223> OTHER INFORMATION: ANTI MYCN PNA

<400> SEQUENCE: 20
cgtcgatttc ttcctc 16

-continued

<210> SEQ ID NO 21
<211> LENGTH: 16
<212> TYPE: DNA
<213> ORGANISM: Artificial
<220> FEATURE:
<223> OTHER INFORMATION: ANTI MYCN PNA

<400> SEQUENCE: 21
ctcgagtttg actcgc 16

<210> SEQ ID NO 22
<211> LENGTH: 16
<212> TYPE: DNA
<213> ORGANISM: Artificial
<220> FEATURE:
<223> OTHER INFORMATION: ANTI MYCN PNA

<400> SEQUENCE: 22
gcgcctcccc tgattt 16

<210> SEQ ID NO 23
<211> LENGTH: 16
<212> TYPE: DNA
<213> ORGANISM: Artificial
<220> FEATURE:
<223> OTHER INFORMATION: ANTI MYCN PNA

<400> SEQUENCE: 23
atatcccccg agcttc 16

<210> SEQ ID NO 24
<211> LENGTH: 16
<212> TYPE: DNA
<213> ORGANISM: Artificial
<220> FEATURE:
<223> OTHER INFORMATION: ANTI MYCN DNA/LNA

<400> SEQUENCE: 24
atgccgggca tgatct 16

<210> SEQ ID NO 25
<211> LENGTH: 16
<212> TYPE: DNA
<213> ORGANISM: Artificial
<220> FEATURE:
<223> OTHER INFORMATION: ANTI MYCN DNA/LNA

<400> SEQUENCE: 25
atgccgggca tgatct 16

<210> SEQ ID NO 26
<211> LENGTH: 19
<212> TYPE: RNA
<213> ORGANISM: Artificial
<220> FEATURE:
<223> OTHER INFORMATION: SENSE OLIGONUCLEOTIDE siMYCN (795)

<400> SEQUENCE: 26
ugaagaugau gaagaggaa 19

<210> SEQ ID NO 27
<211> LENGTH: 19
<212> TYPE: RNA
<213> ORGANISM: Artificial
<220> FEATURE:
<223> OTHER INFORMATION: SENSE OLIGONUCLEOTIDE siMYCN (799)

<400> SEQUENCE: 27
gaugaugaag aggaagaug 19

<210> SEQ ID NO 28
<211> LENGTH: 19
<212> TYPE: RNA
<213> ORGANISM: Artificial
<220> FEATURE:
<223> OTHER INFORMATION: SENSE OLIGONUCLEOTIDE siMYCN (801)

<400> SEQUENCE: 28
ugaugaagag gaagaugaa 19

<210> SEQ ID NO 29
<211> LENGTH: 19
<212> TYPE: RNA
<213> ORGANISM: Artificial
<220> FEATURE:
<223> OTHER INFORMATION: SENSE OLIGONUCLEOTIDE siMYCN (808)

<400> SEQUENCE: 29
gaggaagaug aagaggaag 19

<210> SEQ ID NO 30
<211> LENGTH: 19
<212> TYPE: RNA
<213> ORGANISM: Artificial
<220> FEATURE:
<223> OTHER INFORMATION: SENSE OLIGONUCLEOTIDE siMYCN (810)

<400> SEQUENCE: 30
ggaagaugaa gaggaagaa 19

<210> SEQ ID NO 31
<211> LENGTH: 18
<212> TYPE: DNA
<213> ORGANISM: Artificial
<220> FEATURE:
<223> OTHER INFORMATION: ANTISENSE OLIGONUCLEOTIDE MYCN-PTO (1)

<400> SEQUENCE: 31
cgtggagcag ctcggcat 18

<210> SEQ ID NO 32
<211> LENGTH: 18
<212> TYPE: DNA
<213> ORGANISM: Artificial
<220> FEATURE:
<223> OTHER INFORMATION: ANTISENSE OLIGONUCLEOTIDE MYCN-PTO (763)

<400> SEQUENCE: 32
cagggtgtcc tctccgga 18

<210> SEQ ID NO 33
<211> LENGTH: 21
<212> TYPE: DNA
<213> ORGANISM: Artificial
<220> FEATURE:
<223> OTHER INFORMATION: SENSE OLIGONUCLEOTIDE siRNA-2'-OMe-RNA 808

<400> SEQUENCE: 33
gaggaagaug aagaggaagt t 21

<210> SEQ ID NO 34

<211> LENGTH: 21
<212> TYPE: RNA
<213> ORGANISM: Artificial
<220> FEATURE:
<223> OTHER INFORMATION: SENSE OLIGONUCLEOTIDE siRNA-2'F-RNA 808

<400> SEQUENCE: 34
caggaagaug aagaggaagu u 21

<210> SEQ ID NO 35
<211> LENGTH: 21
<212> TYPE: DNA
<213> ORGANISM: Artificial
<220> FEATURE:
<223> OTHER INFORMATION: SENSE OLIGONUCLEOTIDE siRNA-LNA 808

<400> SEQUENCE: 35
gaggaagaug aagaggaagt t 21

<210> SEQ ID NO 36
<211> LENGTH: 21
<212> TYPE: RNA
<213> ORGANISM: Artificial
<220> FEATURE:
<223> OTHER INFORMATION: SENSE OLIGONUCLEOTIDE siRNA-ANA 808

<400> SEQUENCE: 36
caggaagaug aagaggaaga a 21

<210> SEQ ID NO 37
<211> LENGTH: 19
<212> TYPE: DNA
<213> ORGANISM: Artificial
<220> FEATURE:
<223> OTHER INFORMATION: PRIMER MYCN SENSE

<400> SEQUENCE: 37
cgaccacaag gccctcagt 19

<210> SEQ ID NO 38
<211> LENGTH: 21
<212> TYPE: DNA
<213> ORGANISM: Artificial
<220> FEATURE:
<223> OTHER INFORMATION: PRIMER MYCN ANTISENSE

<400> SEQUENCE: 38
tgaccacgtc gatttcttcc t 21

<210> SEQ ID NO 39
<211> LENGTH: 21
<212> TYPE: DNA
<213> ORGANISM: Artificial
<220> FEATURE:
<223> OTHER INFORMATION: PRIMER ACTB SENSE

<400> SEQUENCE: 39
gagcacagag cctcgccttt g 21

<210> SEQ ID NO 40
<211> LENGTH: 21
<212> TYPE: DNA
<213> ORGANISM: Artificial
<220> FEATURE:
<223> OTHER INFORMATION: PRIMER ACTB ANTISENSE

<400> SEQUENCE: 40
accatcacgc cctggtgcct g 21

<210> SEQ ID NO 41
<211> LENGTH: 22
<212> TYPE: DNA
<213> ORGANISM: Artificial
<220> FEATURE:
<223> OTHER INFORMATION: PRIMER GAPDH SENSE

<400> SEQUENCE: 41
ccaatatgat tccacccatg gc 22

<210> SEQ ID NO 42
<211> LENGTH: 22
<212> TYPE: DNA
<213> ORGANISM: Artificial
<220> FEATURE:
<223> OTHER INFORMATION: PRIMER GAPDH ANTISENSE

<400> SEQUENCE: 42
cttgattttg gagggatctc gc 22

<210> SEQ ID NO 43
<211> LENGTH: 16
<212> TYPE: DNA
<213> ORGANISM: Artificial
<220> FEATURE:
<223> OTHER INFORMATION: MODIFIED SEQ ID NO: 5

<400> SEQUENCE: 43
gctgagtcga tgcgtg 16

<210> SEQ ID NO 44
<211> LENGTH: 16
<212> TYPE: DNA
<213> ORGANISM: Artificial
<220> FEATURE:
<223> OTHER INFORMATION: MODIFIED SEQ ID NO: 5

<400> SEQUENCE: 44
gctgagtgga tgcgtg 16

<210> SEQ ID NO 45
<211> LENGTH: 16
<212> TYPE: DNA
<213> ORGANISM: Artificial
<220> FEATURE:
<223> OTHER INFORMATION: MODIFIED SEQ ID NO: 5

<400> SEQUENCE: 45
gctgggtcga tgcggg 16

<210> SEQ ID NO 46
<211> LENGTH: 16
<212> TYPE: DNA
<213> ORGANISM: Artificial
<220> FEATURE:
<223> OTHER INFORMATION: MODIFIED SEQ ID NO: 5

<400> SEQUENCE: 46
gttgggtgga tgtggg 16

<210> SEQ ID NO 47
<211> LENGTH: 7
<212> TYPE: PRT

-continued

<213> ORGANISM: Artificial
<220> FEATURE:
<223> OTHER INFORMATION: CARRIER PEPTIDE

<400> SEQUENCE: 47

Pro Lys Lys Lys Arg Lys Val
1               5

<210> SEQ ID NO 48
<211> LENGTH: 7
<212> TYPE: PRT
<213> ORGANISM: Artificial
<220> FEATURE:
<223> OTHER INFORMATION: CARRIER PEPTIDE

<400> SEQUENCE: 48

Val Lys Arg Lys Lys Lys Pro
1               5

<210> SEQ ID NO 49
<211> LENGTH: 6
<212> TYPE: PRT
<213> ORGANISM: Artificial
<220> FEATURE:
<223> OTHER INFORMATION: CARRIER PEPTIDE

<400> SEQUENCE: 49

Lys Lys Lys Lys Lys Lys
1               5

<210> SEQ ID NO 50
<211> LENGTH: 7
<212> TYPE: PRT
<213> ORGANISM: Artificial
<220> FEATURE:
<223> OTHER INFORMATION: CARRIER PEPTIDE

<400> SEQUENCE: 50

Pro Lys Arg Lys Arg Lys Val
1               5

<210> SEQ ID NO 51
<211> LENGTH: 7
<212> TYPE: PRT
<213> ORGANISM: Artificial
<220> FEATURE:
<223> OTHER INFORMATION: CARRIER PEPTIDE

<400> SEQUENCE: 51

Lys Arg Lys Arg Lys Arg Lys
1               5

<210> SEQ ID NO 52
<211> LENGTH: 6
<212> TYPE: PRT
<213> ORGANISM: Artificial
<220> FEATURE:
<223> OTHER INFORMATION: CARRIER PEPTIDE

<400> SEQUENCE: 52

Lys Lys Lys Arg Lys Val
1               5

<210> SEQ ID NO 53
<211> LENGTH: 6
<212> TYPE: PRT
<213> ORGANISM: Artificial

<220> FEATURE:
<223> OTHER INFORMATION: CARRIER PEPTIDE

<400> SEQUENCE: 53

Pro Lys Lys Lys Arg Lys
1 5

<210> SEQ ID NO 54
<211> LENGTH: 5
<212> TYPE: PRT
<213> ORGANISM: Artificial
<220> FEATURE:
<223> OTHER INFORMATION: CARRIER PEPTIDE

<400> SEQUENCE: 54

Lys Lys Lys Arg Lys
1 5

<210> SEQ ID NO 55
<211> LENGTH: 4
<212> TYPE: PRT
<213> ORGANISM: Artificial
<220> FEATURE:
<223> OTHER INFORMATION: CARRIER PEPTIDE

<400> SEQUENCE: 55

Arg Arg Arg Arg
1

<210> SEQ ID NO 56
<211> LENGTH: 12
<212> TYPE: PRT
<213> ORGANISM: Artificial
<220> FEATURE:
<223> OTHER INFORMATION: CARRIER PEPTIDE

<400> SEQUENCE: 56

Pro Lys Lys Lys Arg Lys Val His His His His His
1 5 10

<210> SEQ ID NO 57
<211> LENGTH: 19
<212> TYPE: RNA
<213> ORGANISM: Artificial
<220> FEATURE:
<223> OTHER INFORMATION: ANTISENSE OLIGONUCLEOTIDE siMYCN (795)

<400> SEQUENCE: 57
uuccucuuca ucaucuuca 19

<210> SEQ ID NO 58
<211> LENGTH: 19
<212> TYPE: RNA
<213> ORGANISM: Artificial
<220> FEATURE:
<223> OTHER INFORMATION: ANTISENSE OLIGONUCLEOTIDE siMYCN (799)

<400> SEQUENCE: 58
caucuuccuc uucaucauc 19

<210> SEQ ID NO 59
<211> LENGTH: 19
<212> TYPE: RNA
<213> ORGANISM: Artificial
<220> FEATURE:
<223> OTHER INFORMATION: ANTISENSE OLIGONUCLEOTIDE siMYCN (801)

-continued

<400> SEQUENCE: 59
uucaucuucc ucuucauca 19

<210> SEQ ID NO 60
<211> LENGTH: 19
<212> TYPE: RNA
<213> ORGANISM: Artificial
<220> FEATURE:
<223> OTHER INFORMATION: SENSE OLIGONUCLEOTIDE siMYCN (808)

<400> SEQUENCE: 60
cuuccucuuc aucuucuc 19

<210> SEQ ID NO 61
<211> LENGTH: 19
<212> TYPE: RNA
<213> ORGANISM: Artificial
<220> FEATURE:
<223> OTHER INFORMATION: ANTISENSE OLIGONUCLEOTIDE siMYCN (810)

<400> SEQUENCE: 61
uucuuccucu ucaucuucc 19

<210> SEQ ID NO 62
<211> LENGTH: 21
<212> TYPE: DNA
<213> ORGANISM: Artificial
<220> FEATURE:
<223> OTHER INFORMATION: ANTISENSE OLIGONUCLEOTIDE siRNA-2'-OMe-RNA 808

<400> SEQUENCE: 62
cuuccucuuc aucuuccuct t 21

<210> SEQ ID NO 63
<211> LENGTH: 21
<212> TYPE: RNA
<213> ORGANISM: Artificial
<220> FEATURE:
<223> OTHER INFORMATION: ANTISENSE OLIGONUCLEOTIDE siRNA-2'F-RNA 808

<400> SEQUENCE: 63
guuccucuuc aucuuccucu u 21

<210> SEQ ID NO 64
<211> LENGTH: 21
<212> TYPE: DNA
<213> ORGANISM: Artificial
<220> FEATURE:
<223> OTHER INFORMATION: ANTISENSE OLIGONUCLEOTIDE siRNA-LNA 808

<400> SEQUENCE: 64
cuuccucuuc aucuuccuct t 21

<210> SEQ ID NO 65
<211> LENGTH: 21
<212> TYPE: RNA
<213> ORGANISM: Artificial
<220> FEATURE:
<223> OTHER INFORMATION: ANTISENSE OLIGONUCLEOTIDE siRNA-ANA 808

<400> SEQUENCE: 65
guuccucuuc aucuuccuca a 21

<210> SEQ ID NO 66
<211> LENGTH: 16

-continued

<212> TYPE: DNA
<213> ORGANISM: Artificial
<220> FEATURE:
<223> OTHER INFORMATION: ANTI MYCN PNA

<400> SEQUENCE: 66
tcgggagcag tgggca 16

<210> SEQ ID NO 67
<211> LENGTH: 16
<212> TYPE: DNA
<213> ORGANISM: Artificial
<220> FEATURE:
<223> OTHER INFORMATION: ANTI MYCN PNA

<400> SEQUENCE: 67
gcgggtcgcg ggcacg 16

<210> SEQ ID NO 68
<211> LENGTH: 16
<212> TYPE: DNA
<213> ORGANISM: Artificial
<220> FEATURE:
<223> OTHER INFORMATION: ANTI MYCN PNA

<400> SEQUENCE: 68
tggaggtcgg cgccgg 16

<210> SEQ ID NO 69
<211> LENGTH: 16
<212> TYPE: DNA
<213> ORGANISM: Artificial
<220> FEATURE:
<223> OTHER INFORMATION: ANTI MYCN PNA

<400> SEQUENCE: 69
tcggcgggag gtaagg 16

<210> SEQ ID NO 70
<211> LENGTH: 16
<212> TYPE: DNA
<213> ORGANISM: Artificial
<220> FEATURE:
<223> OTHER INFORMATION: ANTI MYC PNA

<400> SEQUENCE: 70
ctcagaggct tggcgg 16

<210> SEQ ID NO 71
<211> LENGTH: 16
<212> TYPE: DNA
<213> ORGANISM: Artificial
<220> FEATURE:
<223> OTHER INFORMATION: ANTI MYC PNA

<400> SEQUENCE: 71
gcggccggct agggtg 16

<210> SEQ ID NO 72
<211> LENGTH: 16
<212> TYPE: DNA
<213> ORGANISM: Artificial
<220> FEATURE:
<223> OTHER INFORMATION: ANTI MYC PNA

<400> SEQUENCE: 72

-continued cggccggcta gggtgg 16

<210> SEQ ID NO 73
<211> LENGTH: 16
<212> TYPE: DNA
<213> ORGANISM: Artificial
<220> FEATURE:
<223> OTHER INFORMATION: ANTI MYC PNA

<400> SEQUENCE: 73
cgacggcggt ggcggg 16

<210> SEQ ID NO 74
<211> LENGTH: 16
<212> TYPE: DNA
<213> ORGANISM: Artificial
<220> FEATURE:
<223> OTHER INFORMATION: ANTI MYC PNA

<400> SEQUENCE: 74
ggacgggggc ggtgga 16

<210> SEQ ID NO 75
<211> LENGTH: 16
<212> TYPE: DNA
<213> ORGANISM: Artificial
<220> FEATURE:
<223> OTHER INFORMATION: ANTI BIRC5 PNA

<400> SEQUENCE: 75
gcggcggcat gggtgc 16

<210> SEQ ID NO 76
<211> LENGTH: 16
<212> TYPE: DNA
<213> ORGANISM: Artificial
<220> FEATURE:
<223> OTHER INFORMATION: ANTI BIRC5 PNA

<400> SEQUENCE: 76
ggcggcggca tgggtg 16

<210> SEQ ID NO 77
<211> LENGTH: 16
<212> TYPE: DNA
<213> ORGANISM: Artificial
<220> FEATURE:
<223> OTHER INFORMATION: ANTI ALK PNA

<400> SEQUENCE: 77
gcaggagagg acggta 16

<210> SEQ ID NO 78
<211> LENGTH: 16
<212> TYPE: DNA
<213> ORGANISM: Artificial
<220> FEATURE:
<223> OTHER INFORMATION: ANTI ALK PNA

<400> SEQUENCE: 78
caggagagga cggtac 16

<210> SEQ ID NO 79
<211> LENGTH: 16
<212> TYPE: DNA
<213> ORGANISM: Artificial

-continued

```
<220> FEATURE:
<223> OTHER INFORMATION: ANTI ALK PNA

<400> SEQUENCE: 79

ggcaggagag gacggt                                                    16


<210> SEQ ID NO 80
<211> LENGTH: 16
<212> TYPE: DNA
<213> ORGANISM: Artificial
<220> FEATURE:
<223> OTHER INFORMATION: ANTI BCL2 PNA

<400> SEQUENCE: 80

ggatggcgca cgctgg                                                    16


<210> SEQ ID NO 81
<211> LENGTH: 16
<212> TYPE: DNA
<213> ORGANISM: Artificial
<220> FEATURE:
<223> OTHER INFORMATION: ANTI BCL2 PNA

<400> SEQUENCE: 81

gggaaggatg gcgcac                                                    16


<210> SEQ ID NO 82
<211> LENGTH: 16
<212> TYPE: DNA
<213> ORGANISM: Artificial
<220> FEATURE:
<223> OTHER INFORMATION: ANTI BCL2 PNA

<400> SEQUENCE: 82

ccacggtggt ggagga                                                    16


<210> SEQ ID NO 83
<211> LENGTH: 16
<212> TYPE: DNA
<213> ORGANISM: Artificial
<220> FEATURE:
<223> OTHER INFORMATION: ANTI PLK4 PNA

<400> SEQUENCE: 83

acggcaagcg gcggga                                                    16


<210> SEQ ID NO 84
<211> LENGTH: 16
<212> TYPE: DNA
<213> ORGANISM: Artificial
<220> FEATURE:
<223> OTHER INFORMATION: ANTI PLK4 PNA

<400> SEQUENCE: 84

ggacggcaag cggcgg                                                    16
```

OLIGONUCLEOTIDES FOR MODULATING GENE EXPRESSION AND USES THEREOF

This Non-Provisional application is a Divisional of U.S. Ser. No. 14/379,729, filed on Aug. 19, 2014, which is a U.S. National Stage of PCT/IB2013/051410 filed on Feb. 21, 2013, which claims priority to and the benefit of Italian Application No. MI2012A000275 filed on Feb. 24, 2012, the contents of which are incorporated herein by reference in their entireties.

The present invention relates to oligonucleotides for modulating the expression of a gene, in particular for modulating a gene responsible for a pathology of genetic, tumoural or viral origin.

Furthermore, the present invention relates to the use of said oligonucleotides, possibly chemically modified, for the treatment and/or the diagnosis of said diseases.

Oligonucleotides are short sequences of natural RNA or DNA nucleic acids or of synthetic nucleic acids, e.g. PNA (Peptide Nucleic Acid), LNA (Locked Nucleic Acid) and morpholinos.

Oligonucleotides have experimentally demonstrated to be very effective in modulating the expression of a gene at the level of both transcription and translation. Because of this ability, oligonucleotides represent a valid means for the treatment of numerous pathologies, in particular diseases of genetic, tumoural or viral origin.

Modulating the expression of a gene can imply inhibiting or activating it.

For example, oligonucleotides are known which are capable of inhibiting the transcription of a gene by forming a complementary bond with the antisense strand of the gene (Hélène C, Bioch Bioph Acta 1990, 1049(2):99-125) or modifying the state of the chromatin in the regulatory regions of the gene of interest (Rossi J J, Nat Chem Biol 2007, 3(3):136-7). Other oligonucleotides are capable of inhibiting gene translation, for example, via a complementary bond with the target Messenger RNA (mRNA). In the case of single-stranded oligonucleotides, this bond causes enzymatic degradation of the mRNA by the RNase H complex. In the case in which the oligonucleotides are molecules of double-stranded "interfering" RNA, the complementary bond of the oligonucleotides with the target mRNA causes degradation of the messenger by the "slicer" enzyme of the RISC complex. In the latter case, the oligonucleotides can also be oligonucleotides equivalent to an endogenous microRNA capable of associating, by virtue of imperfect complementarity, with the 3'UTR region (3' untranslated region) of the target mRNA, causing the translation of that mRNA to be blocked.

Oligonucleotides can also induce the activation of a gene or an increase in the transcription thereof, for example via a complementary bond with long antisense non-coding RNA (Morris K V, Epigenetics, 2009, 4(5): 296-301), or by inhibiting the complementary microRNA, with a consequent increase in the translation of the target mRNA of the microRNA.

Oligonucleotides can be chemically modified with the aim of increasing their effectiveness in therapeutic and/or diagnostic terms. For example, an oligonucleotide can be modified in order to improve its specificity and/or the force with which it pairs with the complementary sequence, or else an oligonucleotide can be modified in order to make it less sensitive to enzymatic degradation, to improve its pharmacokinetic/pharmacodynamic profile, or to facilitate its passage through cell membranes.

In addition to oligonucleotides of natural nucleic acids (i.e. short sequences of DNA and/or RNA), there exist oligonucleotides of synthetic nucleic acids, e.g. peptide nucleic acids (PNA) and locked nucleic acids (LNA), which have been greatly studied and characterized, above all with the aim of modulating the expression of a gene by means of a an antigene strategy (i.e. designed to strike the gene directly). PNA and LNA oligonucleotides, like all modified oligonucleotides, are in general much more chemically stable than DNA or RNA oligonucleotides. Their stability can be further improved by synthesizing chimera oligonucleotides. A chimera oligonucleotide is, for example, an oligonucleotide sequence in which both classic monomers (deoxyribonucleotides or ribonucleotides) and synthetic nucleobases (monomers), for example LNA monomers, are inserted.

LNAs are used with an antisense strategy to silence genes by inhibiting the transcript of the target gene (Braasch D A, Nucl Acids Res, 2002, 30(23):5160-7). Alternatively, LNA oligonucleotides can also be used in an antigene strategy, as was done by Smith and colleagues (Ge R, Faseb J, 2007, 1902-14), who designed the oligonucleotide sequence in such a way as to enable interaction on both strands of the nucleic acid by means of a "strand invasion" mechanism, so as to form a "Z-shaped" structure (defined as "Zorro" oligonucleotides).

PNA oligonucleotides are enzymatically more stable when compared with other oligonucleoside structures. PNAs can bind to double-stranded DNA (DNAds) through "strand invasion", or can pair, in a complementary manner, with a molecule of single-stranded DNA (DNAss), or else they can bind to strands of RNA, giving rise to a hybrid double-helix PNA/DNA or PNA/RNA structure which is thermodynamically very stable compared to "homoduplex" structures (such as a DNA/DNA double strand).

PNAs represent a highly advantageous system for modulating the expression of a gene, above all using an antigene strategy. In fact, it has been demonstrated that PNAs exhibit high specificity for the target sequences and thus enable the expression of the protein to be inhibited in an efficient manner.

Therefore, PNAs represent a promising therapeutic approach for the treatment of genetic or viral diseases.

The only disadvantage of PNAs is the fact that they have a limited ability to pass through cell membranes. However, this limitation has been solved by conjugating oligonucleotides in general, and PNAs in particular, with molecules capable of rendering the passage through cell membranes more effective (carriers).

In fact, oligonucleotides, and PNAs specifically, can in general be administered using carriers (or "tags") conjugated to them, for example peptide sequences with a length varying from 1 to 30 amino acids.

One particular application of oligonucleotides regards modulating the expression of the genes which are activated or repressed in tumours.

It is well known that tumours are caused by the dysregulation of various genes. Usually, the damage affects proto-oncogenes (or also simply oncogenes) like the MYC genes (tra cui MYC, MYCN, MYCL1), survivin (BIRC5), BCL2, PLK4, ALK and PKM2, which are activated or overexpressed in the tumour. Moreover, in a tumour, antitumour or oncosuppressor genes such as caspase-8 and RASSF1 are usually also inactivated.

In particular, the oncogenes of the MYC family are involved in the development of numerous human tumours and are among the genes most responsible for the onset and progression of neoplasms. Amplification and/or overexpression of these genes is almost always associated with tumours, both of the paediatric type (e.g. neuroblastoma, medulloblastoma and rhabdomyosarcoma) and adult type (e.g. small cell lung cancer, or glioblastoma) (Pession A, Cur Cancer Drug Target, 2005, 5(4):273-83). In fact, they act by means of mechanisms which are fundamental for tumour growth, such as induction of cell proliferation, resistance to apoptosis, formation of metastasis and resistance to chemotherapy drugs.

Many oligonucleotides with an antitumour effect are known in the literature.

For example, there exist oligonucleotides which are directed against the MYC, MYCN, BCL2, BIRC5 genes in antisense strategies (EV Prochownik, Exp Rev Antic Ther 2004, 4(2):289-302; Felsher D W, Drug News Persp, 2003, 16(6):370-4; CF Bennet, Exp Opin Investig Drugs, 1999, 8(3):237-53) or oligonucleotides directed against MYCN and MYC with an antigene effect (LC Boffa, Oligonucleotides 2005, 15(2):85-93).

DNA-based phosphorothioate antisense oligonucleotides have also been generated with the aim of inhibiting the translation of the MYCN gene into neuroblastoma cells (Burkhart C A, JNCI, 2003, 95(18):1394-403) and antisense oligonucleotides have been generated through "small interfering RNA (siRNA)" to inhibit the translation of the MYCN gene into neuroblastoma cells (Kang J H, Bioch Bioph Res Com, 2006, 351(1):192-197).

However, there is still a strong felt need to identify further oligonucleotides capable of modulating the expression of a gene in an increasingly specific and selective manner so as to be able to have a potent therapeutic and/or antitumour effect.

In order to obtain oligonucleotides utilizable as therapeutic and/or diagnostic means, it is necessary to identify the sequences of a target gene, or a target messenger RNA and/or their respective regulatory sequences which are capable of determining a significant and selective modulation effect on the expression of the gene itself in terms of both transcription and translation.

Thus there is also a felt need to define the general rules governing the process of identifying—within the sequence of a gene, or the sequence of a messenger RNA or the regulatory sequences thereof—the oligonucleotide sequences that are most promising for the purposes of modulating the transcription/translation of the gene itself.

The needs in this sector as just described are met by the present invention, which, according to a first aspect, relates to an oligonucleotide for modulating the expression of a gene, comprising 6-30 nucleotides (monomers), preferably 12-24 nucleotides, said oligonucleotide being characterized by a sequence comprising at least one group of at least two consecutive guanines. The oligonucleotide having the sequence SEQ ID NO: 1 is understood as being excluded from the definition just given.

In the case of natural nucleic acids (DNA and RNA), each monomer (nucleotide) consists of a nitrogenous base, a sugar and a triphosphate. The base is selected from among adenine, guanine, thymine, cytosine and uracil (only in RNA). The sugar is deoxyribose in the case of DNA and ribose in the case of RNA. The monomers are linked in the polymer by a phosphodiester bond.

Preferably, the oligonucleotide of the present invention comprises a sequence comprising at least one group of at least three consecutive guanines. The oligonucleotide having the sequence SEQ ID NO: 1 is understood as being excluded from this definition.

More preferably, the oligonucleotide of the present invention comprises a sequence comprising at least one group of at least four consecutive guanines.

Even more preferably, the oligonucleotide of the present invention comprises a sequence comprising at least one group of at least five consecutive guanines.

Particularly preferred for the purposes of the present invention is an oligonucleotide comprising a sequence comprising at least one group of at least six consecutive guanines.

In some embodiments of the invention, the oligonucleotide comprises a sequence comprising at least one group consisting of two to six consecutive guanines.

In further embodiments the at least one group of guanines preferably comprises at least two groups of at least two consecutive guanines.

Alternatively the at least one group of guanines preferably comprises at least one group of at least two consecutive guanines and at least one group of at least three consecutive guanines.

In further embodiments the at least one group of guanines preferably comprises at least three groups of at least two consecutive guanines.

In further embodiments the at least one group of guanines preferably comprises at least four, five or six groups of at least two consecutive guanines.

Alternatively the at least one group of guanines preferably comprises at least one group of at least two consecutive guanines and at least two groups of at least three consecutive guanines.

Alternatively the at least one group of guanines preferably comprises at least one group of at least three consecutive guanines and at least two groups of at least two consecutive guanines.

Alternatively the at least one group of guanines preferably comprises at least one group of at least two consecutive guanines, at least one group of at least three consecutive guanines and/or at least one group of six consecutive guanines.

In general, the oligonucleotides of the present invention are perfectly complementary to the target sequence and, preferably, the groups of consecutive guanines can be consecutive to one another so that, for example, three groups of 2 consecutive guanines is a group of 6 consecutive guanines. Alternatively, the groups of consecutive guanines can be spaced apart by at least one nucleotide.

In general, the at least one group of at least two consecutive guanines according to the present invention can be located near the 5' end of the oligonucleotide, or near the 3' end of the oligonucleotide, or else it can be located at the centre of the oligonucleotide sequence.

In preferred embodiments of the present invention said oligonucleotide is conjugated, preferably at its 3' and/or 5' end, with a carrier sequence, which is preferably a short amino acid sequence.

Said short amino acid sequence (carrier) preferably consists of a number of amino acids ranging from 1 to 30, preferably 1 to 10, even more preferably 1 to 7. The amino acids can be in L or D form, preferably in D form.

The carriers that are preferred for the purposes of the present invention are selected from the group consisting of: SEQ ID NO: 47 (PKKKRKV); SEQ ID NO: 48 (VKRKKKP); SEQ ID NO: 49 (KKKKKK); SEQ ID NO: 50 (PKRKRKV); SEQ ID NO: 51 (KRKRKRK); SEQ ID NO: 52 (KKKRKV); SEQ ID NO: 53 (PKKKRK); SEQ ID NO: 54 (KKKRK); SEQ ID NO: 55 (RRRR) and SEQ ID NO: 56 (PKKKRKVHHHHH).

The carrier that is particularly preferred for the purposes of the present invention is the peptide having the SEQ ID NO: 47.

In the context of the present invention, "carrier" means a peptide capable of favourably modifying the pharmacokinetic and/or pharmacodynamic profile and/or cellular and/or nuclear penetration of an oligonucleotide.

In the context of the present invention, "modulating the expression of a gene" means inhibiting or activating (increasing) the expression of a gene. Said inhibition or activation of (increase in) gene expression can occur on a transcription or translation level.

The inhibition or activation of gene expression can be achieved on a transcription level by means of oligonucleotides which act with an antigene mechanism (or antigene oligonucleotide, i.e. directed against the antisense strand of the gene, that is, antigene strategy). Alternatively, the inhibition of gene expression can be achieved on a translation level using oligonucleotides which act through an antisense mechanism (or antisense oligonucleotide, i.e. directed against the messenger, that is, antisense strategy), whereas an increase in expression on a translation level can be achieved by inhibiting the microRNAs which degrade the messenger RNA.

The parameters or rules or prerequisites that an oligonucleotide must satisfy in order to effectively modulate the expression of a gene, identified by the Applicant and stated above, are valid for any gene whatsoever and can thus be applied, for example, for the purpose of identifying sequences of oligonucleotides which are capable of modulating the expression of the gene(s) responsible for diseases of genetic and/or viral origin or the genes involved in the onset of tumour pathologies.

The oligonucleotides thus identified can be used, preferably as drugs, in therapeutic approaches for the treatment of specific genetic, viral or tumoural diseases.

Alternatively, the oligonucleotides can be utilized for diagnostic purposes.

In fact, the subject matter of the present invention further relates to the use of the oligonucleotides of the invention, possibly chemically modified, for therapeutic and/or diagnostic purposes.

The oligonucleotides of the present invention are short oligonucleotides of 6-30, preferably 12-24 residues (nucleotides or monomers). The oligonucleotides can consist of a natural nucleic acid base, for example DNA or RNA, or a synthetic nucleic acid base, for example PNA, LNA or morpholino. Alternatively, the oligonucleotides can comprise a combination of DNA, RNA and/or synthetic nucleic acids, preferably PNA or LNA (hybrid or chimeric oligonucleotides). Moreover, the oligonucleotides can be single- or double-stranded.

In some embodiments of the present invention, the oligonucleotides can be chemically modified, for example for the purpose of improving their therapeutic and/or diagnostic effectiveness.

In preferred embodiments of the present invention, the oligonucleotides can be PNA molecules with a backbone in which the carbon in the alpha position ($C_{alpha(\alpha)}$) is bound to substituents other than the typical hydrogen atom of glycine. For example, instead of the side chain of glycine the side chain of another amino acid of natural or synthetic origin can be used, preferably selected from the group consisting in: arginine, lysine, histidine, leucine, isoleucine, tyrosine, asparagine, serine, threonine, glutamine, valine, alanine, cysteine, methionine, phenylalanine, glutamate, aspartate, proline, tryptophan and ornithine. Said amino acid can be of the dextrorotatory configuration (D) or the levorotatory configuration (L).

In other preferred embodiments of the invention, the oligonucleotides are: mutually complementary single- or double-stranded RNA molecules (the mutually complementary double-stranded RNA molecules are defined as siRNA, acronym of "small interfering RNA").

In some embodiments, said "small interfering RNA" comprises RNA monomers (ribonucleotides) and at least one modified monomer in the ribose 2' position, preferably a 2'-O-methoxyethyl, 2'-O-methyl or 2'-fluoro monomer; or said "small interfering RNA" comprises RNA monomers (ribonucleotides) and at least one monomer of a synthetic nucleic acid preferably selected from among: LNA, Methylphosphonate LNA, BNA (bridged nucleic acid), UNA (unlocked nucleic acid), ENA (ethylene-bridged nucleic acid), ANA (arabinose nucleic acid) and F-ANA (fluoro-arabinoside nucleic acid).

In preferred embodiments, said "small interfering RNA" is designed in such a way that at the ends of the complementary double strand, only one of the two strands has at least one, preferably two, monomers of natural or synthetic nucleic acids which protrude, i.e. are not paired. In further embodiments, natural or synthetic protruding nucleic acids are preferably selected from among: a 2'-O-methoxyethyl, 2'-O-methyl and 2'-fluoro monomer or a monomer of: LNA, Methylphosphonate LNA, BNA, UNA (unlocked nucleic acid), ENA (ethylene-bridged nucleic acid), ANA (arabinose nucleic acid) and F-ANA (fluoro-arabinoside nucleic acid).

In further embodiments, the oligonucleotides are defined as hybrid or chimeric and are preferably single- or double-stranded, comprising RNA monomers (ribonucleotides) and LNA monomers (this oligonucleotide is represented as RNA/LNA). Alternatively, the hybrid oligonucleotides can comprise the RNA monomers (ribonucleotides) and at least one RNA monomer selected from among: a 2'-O-Methoxyethyl (MOE) monomer, a 2'-O-methyl monomer and a 2'-fluoro monomer; or the hybrid oligonucleotides can comprise RNA monomers (ribonucleotides) and at least one monomer of a synthetic nucleic acid preferably selected from among: LNA, methylphosphonate LNA, UNA (unlocked nucleic acid), BNA, ENA (ethylene nucleic acid), ANA (arabinose nucleic acid) and F-ANA (fluoro-arabinoside nucleic acid).

In a further embodiment, the oligonucleotides based on single- or double-stranded RNA can comprise classic ribonucleotides (i.e. not chemically modified) and ribonucleotides or deoxyribonucleotides which have been modified at the level of the phosphodiester bond, for example by means of a phosphorothioate bond, or DNG (deoxyribonucleic guanidine), RNG (ribonucleic guanidine), GNA (glycerol nucleic acid), G-PNA (gamma-PNA) or PMO (Morpholino).

In preferred embodiments of the invention, the oligonucleotides are chimeric single-stranded sequences comprising DNA monomers (deoxyribonucleotides) and LNA monomers.

For an antigene strategy, which means modulating the expression of a gene on the transcription level, one can preferably employ:

- PNA-based oligonucleotides, optionally conjugated with a carrier (generally consisting of 1 to 30 residues), preferably at the 3' end and/or 5'; or
- PNA-based oligonucleotides, said PNA comprising at least one alpha carbon (C-alpha) of the backbone with a substituent other than the H atom of the canonical glycine; or

- single-stranded oligonucleotides comprising RNA monomers (the classic ribonucleotides) and optionally at least one modified nucleotide (monomer) (for example a 2'-O-Methyl RNA monomer, a 2'-Fluoro RNA monomer), or at least one monomer of a nucleic acid selected from among: LNA, methylphosphonate LNA, BNA, UNA, GNA, ANA, FANA, ENA, DNG and RNG, or a ribonucleotide modified at the level of the phosphodiester bond; or
- mutually complementary double-stranded RNA-based oligonucleotides (siRNA); or
- partially complementary double-stranded chimeric oligonucleotides comprising RNA monomers (the classic ribonucleotides) and at least one LNA monomer; or
- double-stranded chimeric oligonucleotides comprising RNA monomers (the classic ribonucleotides) and at least one 2'-O-(2-Methoxyethyl) RNA monomer; or
- single-stranded chimeric oligonucleotides comprising DNA monomers (the classic deoxyribonucleotides) and at least one LNA monomer; or
- oligonucleotides comprising DNA monomers (the classic deoxyribonucleotides) and at least one 2'-Fluoro RNA monomer or at least one monomer of a nucleic acid selected from among: LNA, Methylphosphonate LNA, BNA, UNA, GNA, ENA, ANA, FANA, DNG and RNG.

For an antisense strategy, which means modulating the expression of a gene on a translation level, one can preferably utilize:

- mutually complementary double-stranded oligonucleotides comprising RNA monomers (the classic ribonucleotides) (siRNA); or
- single-stranded oligonucleotides comprising RNA monomers (the classic ribonucleotides) and at least one RNA monomer modified at the ribose level and/or at the level of the phosphodiester bond; or
- single-stranded chimeric oligonucleotides comprising DNA monomers (the classic deoxyribonucleotides) and at least one phosphorothioate DNA monomer; or
- double-stranded chimeric oligonucleotides comprising RNA monomers (the classic ribonucleotides) and at least one 2'-O-(2-Methoxyethyl) RNA monomer; or
- double-stranded chimeric oligonucleotides comprising RNA monomers (the classic ribonucleotides) and at least one 2'O-methylate RNA monomer; or
- double-stranded chimeric oligonucleotides comprising RNA monomers (the classic ribonucleotides) and at least one 2'-fluoro RNA monomer; or
- double-stranded chimeric oligonucleotides comprising RNA monomers (the classic ribonucleotides) and at least one LNA monomer; or
- double-stranded chimeric oligonucleotides comprising RNA monomers (the classic ribonucleotides) and at least one arabinoside RNA monomer; or
- single-stranded chimeric oligonucleotides comprising DNA monomers (the classic deoxyribonucleotides) and at least one LNA monomer; or
- single-stranded oligonucleotides comprising morpholino monomers; or
- PNA-based oligonucleotides, said PNA comprising at least one alpha carbon (C-alpha) of the backbone with a substituent other than the H atom of the canonical glycine; preferably the substituent is the side chain of arginine or lysine; or
- oligonucleotides comprising DNA monomers (the classic deoxyribonucleotides) and at least one monomer of a nucleic acid selected from among: PNA, LNA, LNA methylphosphonate, BNA, UNA, GNA, ENA, DNG and RNG.

Preferably, the oligonucleotides of the present invention are directed against a gene involved in the development of a disease of genetic and/or viral origin or a tumour. Said gene is preferably selected from the group consisting of: genes of the MYC family (preferably MYC, MYCN, MYCL1), survivin genes (BIRC5), BCL2, PLK4, ALK, PKM2, caspase-8 and RASSF1.

In particular, the oligonucleotides of the present invention are directed against the genes of the MYC family, preferably against MYCN.

Said oligonucleotides are preferably selected from the group consisting of: SEQ ID NO: 2-15, 66-84, SEQ ID NO: 24, 25, 31 and 32, the pair of complementary oligonucleotides having SEQ ID NO: 26 and 57, the pair of complementary oligonucleotides having SEQ ID NO: 27 and 58, the pair of complementary oligonucleotides having SEQ ID NO: 28 and 59, the pair of complementary oligonucleotides having SEQ ID NO: 29 and 60, the pair of complementary oligonucleotides having SEQ ID NO: 30 and 61, the pair of complementary oligonucleotides having SEQ ID NO: 33 and 62, the pair of complementary oligonucleotides having SEQ ID NO: 34 and 63, the pair of complementary oligonucleotides having SEQ ID NO: 35 and 64 and the pair of complementary oligonucleotides having SEQ ID NO: 36 and 65.

In some embodiments, said oligonucleotides are PNA oligonucleotides, preferably said PNAs are directed against MYCN.

In preferred embodiments the PNAs are selected from the group consisting of: SEQ ID NO: 2-15.

In further preferred embodiments the PNAs are selected from the group consisting of: SEQ ID NO: 66-84.

In further preferred embodiments the PNAs are selected from the group consisting of: SEQ ID NO: 2-15, 66-84.

Preferably, the PNA oligonucleotides are selected from the group consisting of: SEQ ID NO: 2-13, more preferably SEQ ID NO: 2-8, even more preferably SEQ ID NO: 2-6. The PNA oligonucleotide that is particularly preferred for the purposes of the present invention is SEQ ID NO: 5.

Preferably, SEQ ID NO: 5 is conjugated at the 5' or 3' end with SEQ ID NO: 47. More preferably, SEQ ID NO: 47 consists of amino acids in D form.

The PNAs SEQ ID NO: 2-15 are preferably directed against MYCN and, more preferably, they modulate the expression of MYCN with an antigene strategy.

The PNAs SEQ ID NO: 66-69 are also preferably directed against MYCN and, more preferably, they modulate the expression of MYCN with an antigene strategy.

The PNAs SEQ ID NO: 70-74 are preferably directed against MYC and, more preferably, they modulate the expression of MYC with an antigene strategy.

The PNAs SEQ ID NO: 75, 76 are preferably directed against BIRC5 and, more preferably, they modulate the expression of BIRC5 with an antigene strategy.

The PNAs SEQ ID NO: 77-79 are preferably directed against ALK and, more preferably, they modulate the expression of ALK with an antigene strategy.

The PNAs SEQ ID NO: 80-82 are preferably directed against BCL2 and, more preferably, they modulate the expression of BCL2 with an antigene strategy.

The PNAs SEQ ID NO: 83, 84 are preferably directed against PLK4 and, more preferably, they modulate the expression of PLK4 with an antigene strategy.

In a further embodiment, said oligonucleotides are double-stranded and preferably comprise RNA monomers. Preferably said oligonucleotides are directed against MYCN.

Alternatively, said double-stranded RNA oligonucleotides are selected from the group consisting of: the pair of complementary oligonucleotides having SEQ ID NO: 26 and 57, the pair of complementary oligonucleotides having SEQ ID NO: 27 and 58, the pair of complementary oligonucleotides having SEQ ID NO: 28 and 59, the pair of complementary oligonucleotides having SEQ ID NO: 29 and 60 and the pair of complementary oligonucleotides having SEQ ID NO: 30 and 61. Said oligonucleotides are preferably directed against MYCN. More preferably, they modulate the expression of the gene through an antisense strategy.

In further embodiments, said oligonucleotides are DNA-LNA chimeric oligonucleotides, preferably said oligonucleotides are directed against MYCN.

In preferred embodiments, said DNA-LNA chimeric oligonucleotides are selected from the group consisting of: SEQ ID NO: 24 and 25.

SEQ ID NO: 24 and 25 are preferably directed against the MYCN gene.

SEQ ID NO: 24 and 25 preferably modulate the gene's expression through an antigene strategy.

In further embodiments, said oligonucleotides are single-stranded chimeric oligonucleotides comprising DNA monomers and/or at least one phosphorothioate DNA monomer. Said oligonucleotides are preferably directed against MYCN. Particularly preferred for the purposes of the present invention are the chimeric oligonucleotides selected from the group consisting of: SEQ ID NO: 31 and 32. SEQ ID NO: 31 and 32 and are preferably directed against the MYCN gene. SEQ ID NO: 31 and 32, preferably, modulate the expression of MYCN through an antisense strategy.

In further embodiments, said oligonucleotides are double-stranded chimeric oligonucleotides comprising RNA monomers and at least one monomer preferably of 2'-O-(2-Methoxyethyl) or 2'-methyl RNA.

Said oligonucleotides are preferably directed against MYCN. Particularly preferred for the purposes of the present invention is the pair of complementary chimeric oligonucleotides having SEQ ID NO: 33 and 62. Said pair of oligonucleotides preferably modulates the expression of the gene through an antisense mechanism.

In further embodiments, said oligonucleotides are double-stranded chimeric oligonucleotides comprising RNA monomers and at least one monomer preferably of 2'-Fluoro RNA. Preferably, said oligonucleotides are directed against MYCN. Particularly preferred for the purposes of the present invention is the pair of complementary chimeric oligonucleotides having SEQ ID NO: 34 and 63. Said pair of oligonucleotides preferably modulates the gene's expression through an antisense mechanism.

In further embodiments, said oligonucleotides are double-stranded chimeric oligonucleotides comprising RNA monomers and at least one LNA monomer.

Said oligonucleotides are preferably directed against MYCN. Particularly preferred for the purposes of the present invention is the pair of complementary chimeric oligonucleotides having SEQ ID NO: 35 and 64. Said pair of oligonucleotides preferably modulates the gene's expression through an antisense mechanism.

In further embodiments, said oligonucleotides are double-stranded chimeric oligonucleotides, comprising RNA monomers and at least one arabinoside RNA monomer.

Preferably, said oligonucleotides are directed against MYCN. Particularly preferred for the purposes of the present invention is the pair of complementary chimeric oligonucleotides having SEQ ID NO: 36 and 65. Said pair of oligonucleotides preferably modulates the gene's expression through an antisense mechanism.

A further aspect of the invention relates to the use of the above-described oligonucleotides for therapeutic and/or diagnostic purposes.

In particular, the oligonucleotides can be used individually or combined together for the treatment of diseases of genetic and/or viral origin, in particular for the treatment of genetic diseases caused either by overexpression or inhibition of a gene, i.e. genetic diseases which require the modulation of the expression of a gene which is overexpressed or inhibited.

The oligonucleotides of the invention are used for the therapeutic treatment of a genetic disease, preferably selected from the group consisting of: Gorlin syndrome, Down syndrome, Feingold syndrome, Hirschsprung's disease, Von Hippel Lindau syndrome, Ataxia Telangiectasia, Li-Fraumeni syndrome, Turcot syndrome, familial tumours and Parkinson's disease.

Furthermore, the oligonucleotides of the invention are used for the therapeutic treatment of tumoural pathologies in children or adults. In particular, the tumours to which reference is made are caused, preferably, by the overexpression of a gene or oncogene selected from the group consisting of: MYC, MYCN, MYCL1, survivin (BIRC5), BCL2, PLK4, ALK and PKM2. Alternatively, the tumours are caused, preferably, by the inhibition (inactivation) of an onco-suppressor or anti-tumour gene and preferably selected from the group consisting of: caspase-8 and RASSF1.

The tumours to which reference is made are preferably selected from the group consisting of: neuroblastoma, retinoblastoma, medulloblastoma, ependymoma, pheochromocytoma, embryonal carcinoma, germ cell tumour, alveolar rabdomyosarcoma, embryonal rabdomiosarcoma, Wilms' tumour, clear cell sarcoma of the kidney, synovial sarcoma, hepatoblastoma, acute lymphoid leukaemia, chronic lymphoid leukaemia, acute lymphoblastic leukaemia, chronic lymphoblastic leukaemia, Burkitt's lymphoma, acute myeloid leukaemia, chronic myeloid leukaemia, acute megakaryoblastic leukaemia, B chronic lymphoid leukaemia, T-cell leukaemia, lymphomas, small cell lung cancer (microcytoma), lung adenocarcinoma, squamous cell lung carcinoma, typical and atypical primary lung cancer, large cell lung carcinoma, large-cell neuroendocrine lung carcinoma, glioblastoma, hepatocarcinoma, basal cell carcinoma, ovarian tumour, breast tumour and colon cancer.

Particularly preferred for the purposes of the present invention are the tumours selected from the group consisting of: neuroblastoma, retinoblastoma, rabdomyosarcoma, Wilms' tumour, medulloblastoma, small cell lung cancer and basal cell carcinoma.

The subject matter of the present invention further relates to a composition comprising at least one oligonucleotide according to the present invention and at least one pharmacologically accepted excipient. Preferably, said at least one oligonucleotide is a PNA, preferably selected from the group consisting of: SEQ ID NO: 2-15, 66-84, preferably SEQ ID NO: 2-13, more preferably SEQ ID NO: 2-8, even more preferably SEQ ID NO: 2-6. The oligonucleotide that is particularly preferred is SEQ ID NO: 5. Preferably, SEQ ID NO: 5 is conjugated at the 5' or 3' end with SEQ ID NO: 47. More preferably, SEQ ID NO: 47 consists of amino acids in the D form.

Said PNA is preferably conjugated at its 5' or 3' end with a carrier which is preferably selected from the group consisting of: SEQ ID NO: 47-56.

The subject matter of the present invention further relates to a combination comprising at least one oligonucleotide according to the present invention, including the oligonucleotide having SEQ ID NO: 1, at least one compound, preferably at least one compound with a pharmacological effect, more preferably a chemotherapeutic agent, and, optionally, at least one pharmacologically accepted excipient.

In preferred embodiments said at least one compound is at least one additional antigene and/or antisense oligonucleotide, or at least one pharmacological agent, or at least one compound of biological or biotechnological origin or deriving from chemical synthesis or combinations thereof. Said compound of biological or biotechnological origin or deriving from chemical synthesis is preferably selected from the group consisting of: a monoclonal antibody, a chemotherapeutic agent, an immunomodulating agent, a growth factor, a cytokine, a peptide, an angiogenesis inhibitor, a tumour growth inhibitor, a steroid hormone and/or a non-steroid hormone and vitamins.

Examples of compounds that are particularly preferred for the purposes of the present invention are selected from the group consisting of: nerve growth factor (NGF), somatostatin, retinoic acid, actinomycin D, asparaginase, bleomycin, busulphan capecitabine, carboplatin, cyclophosphamide, cyclosporine, cisplatin, cytarabine, clorambucil, dacarbazine, daunorubicin, docetaxel, doxorubicin hydrochloride, epirubicin hydrochloride, etoposide, fludarabine phosphate, fluorouracil, gemcitabine, idarubicin hydrochloride, hydroxyurea, ifophosphamide, irinotecan hydrochloride, melphalan, mercaptopurine, methotrexate, mitomycin, mitoxantrone, nutline, oxaliplatin, paclitaxel, procarbazine, raltitrexed, streptozocin, tegafur-uracil, temozolomide, thioguanine, thiotepe, topotecan, vinblastine, vincristine, vindesine and vinorelbine and combinations thereof.

More preferably, the compounds are selected from the group consisting of: carboplatin, cisplatin, etoposide, vincristine, cyclophosphamide and combinations thereof.

The Applicant has found that the administration of at least one oligonucleotide according to the invention in concomitance with at least one compound, preferably at least one chemotherapeutic agent, as described above, makes it possible to reduce the concentration of said compound to be administered, while at the same time guaranteeing an increase in the therapeutic effectiveness and lower toxicity.

The Applicant has found that, under these conditions, the reduction in the concentration of said compound depends on the particular pathology; in particular, the concentration of the chemotherapeutic compound depends on the type of tumour. For some tumours, such as: neuroblastoma, retinoblastoma, medulloblastoma, small cell lung cancer, Wilms' tumour, alveolar rabdomyosarcoma and embryonal rabdomiosarcoma, the concentration of the at least one chemotherapeutic agent, administered in combination with at least one oligonucleotide according to the present invention, can be reduced by up to 10 times while guaranteeing the same therapeutic effect as a normal dose of a chemotherapeutic agent.

Particularly effective as a pharmaceutical combination (in terms of improved therapeutic effect) is the combination of at least one PNA according to the present invention, preferably at least one PNA selected from the group consisting of: SEQ ID NO: 1-15, 66-84, preferably SEQ ID NO: 1-13, more preferably SEQ ID NO: 1-8, more preferably SEQ ID NO: 1-6, even more preferably SEQ ID NO: 1 and/or 5, and at least one compound, preferably a chemotherapeutic agent, more preferably selected from the group consisting of: etoposide (VP16), carboplatin, cisplatin or vincristine, cyclophosphamide and combinations thereof.

Particularly preferred for the purposes of the present invention is a combination selected from among: SEQ ID: NO 1 and carboplatin, or etoposide or cisplatin or vincristine; or SEQ ID: NO 5 and carboplatin or etoposide or cisplatin or vincristine.

Said PNA is preferably conjugated at its 3' and/or 5' end with a carrier, which is preferably selected from the group consisting in: SEQ ID NO: 47-56.

The improvement effect is preferably to be found both when the combination is administered simultaneously and when said at least one compound is administered at successive times, preferably at intervals, more preferably at regular intervals of 3 hours, 6 hours, 12 hours, 24 hours, 48 hours or 72 hours.

In other preferred embodiments, at least one oligonucleotide of the invention, including the oligonucleotide having SEQ ID NO: 1, can be administered conjugated or complexed, preferably with at least one vehicle particle, at least one vehicle polymer or at least one self-assembled vehicle oligonucleotide (also known as aptamers).

In further preferred embodiments, at least one oligonucleotide of the invention, including the oligonucleotide having SEQ ID NO: 1, can be conjugated or complexed and administered with at least one liposomal micelle, at least one micro-particle or at least one nanoparticle such as to favour permeation of the target tissue.

Said particle, usually spherical in shape and used as a means of specific delivery, can be formulated with many different chemical compounds. For example, said particle can be a formulation or co-formulation of polymeric compounds such as: chitosan, hyaluronic acid, polyethylene glycol (PEG), polyethyleneimine (PEI), polylactic acid (PLA), poly(lactic-co-glycolic acid) (PLGA), hydroxyapatite (HAP), polyunsaturated fatty acids, saturated fatty acids, cationic lipids, HAP-PLA, HAP-PLA/PGA and derivatives thereof. In further preferred embodiments, at least one oligonucleotide of the invention can be administered conjugated or complexed, preferably with at least one particle of the previously described type, and at least one ligand or at least one portion of a ligand for a specific receptor of the target cells (such as, for example, GD2, folic acid, TRAIL, NGF), either of chemical or biotechnological origin, may be present in the polymeric membranes as an adjuvant, useful for favouring the internalization of said oligonucleotide of the invention in the target cells.

In further preferred embodiments, at least one oligonucleotide of the invention can be conjugated with at least one ligand or a portion of a ligand (such as, for example, GD2 (ganglioside GD2), folic acid, TRAIL (TNF-RELATED APOPTOSIS-INDUCING LIGAND), NGF (Nerve Growth Factor) specific for a receptor of the target cells.

In further preferred embodiments, at least one oligonucleotide of the invention, including the oligonucleotide having SEQ ID NO: 1, can be administered, on its own or in a combination, in association with at least one further medical application in order to enhance their effectiveness, preferably also by facilitating permeation of the target cells and/or tissues.

Said medical application is preferably selected from the group consisting of: oxygen therapy, magnetotherapy, thermotherapy, electrostimulation, ultrasound, radiotherapy, chemotherapy and phototherapy.

EXAMPLE 1

Chemical Synthesis of the Oligonucleotides.

The chemical synthesis of the oligonucleotides is based on the use of DNA nucleoside phosphoroamidites modified with a protecting group, 4,4'-dimethoxytrityl (DMTr) on 5'-OH and β-cyanoethyl on the 3'-phosphate group; protecting groups are also used for the primary amines (nucleobase heterocycles), which are otherwise too reactive.

The chemical synthesis of DNA oligonucleotides takes place in a 3'-5' direction. Use is made of a CPG (acronym of controlled pore glass) resin or a polystyrene support, functionalized with the first nucleotide base. The synthesis begins with a step of deprotecting the 5'-dimethoxytrityl group using a solution of 3% trichloroacetic acid (TCA) in dichloromethane (DCM). This is followed by activation, using ethylthiotetrazole (ETT) or benzylthiotetrazole (BTT) 0.3M, of the phosphoroamidite corresponding to the second base to be inserted in sequence, which will then be coupled with the previously deprotected 5'OH, thereby forming a phosphodiester bond.

The next step is “capping”, which serves to acetylate the 5'OH groups that have not reacted. Capping is carried out using 2 solutions, one containing tetrahydrofuran (THF)/lutidine/acetic anhydride (8:1:1) and the other containing a 10% solution of methylimidazole in THF. The unstable trivalent bond of the phosphite triesters is stabilized by iodine in a THF/pyridine solution which oxidizes them to pentavalent phosphodiesters.

After oxidization, the cycle is repeated, starting with detritylation of the second unit introduced and so forth. This cycle is repeated for the number of times necessary, depending on how many bases it is desired to insert in sequence. Finally, the final 5'-DMTr group is removed by means of a treatment with an acid at room temperature.

Depending on the protecting groups present on the bases (which in turn depends on the chemistry of the bases selected, PTO, 2'OMe, etc.) it can be left at 55° C. for 16 hours with ammonium hydroxide or at 55° C. for 35 minutes with an ammonium hydroxide/methylamine (AMA) solution in order to deprotect the phosphors by R-elimination of the cyanoethyl groups and remove the protecting groups on the nucleobase heterocycles.

Alternatively, the 5'-DMTr group can be maintained throughout the phase of analysis (HPLC, MS) and preparative chromatography in order to better purify the final product from the by-products and finally removed by means of a treatment with acetic acid The chemical synthesis of RNA oligonucleotides differs from that of DNA oligonucleotides because of the 2'OH group present on the ribose and thus the presence of an additional protecting group for each phosphoroamidite.

Consequently, the synthesis of RNA oligonucleotides requires a longer coupling time and further steps to deprotect that group.

The same protocol as described above is used for the synthesis of oligonucleotides with chemically modified monomers, such as phosphorothioates (PTO), 2'O-Methyl (2'OMe), 2'Fluoro (2'-F), arabinoside nucleic acid (ANA), and locked nucleic acid (LNA).

The details of the specific techniques for each modified base are provided by the company the monomer molecules are purchased from (Link Technologies Ltd.).

The morpholinos were purchased from the manufacturer (Gene Tools, LLC).

The synthesis of PNA oligonucleotides was carried out on a 10 micromole scale, and included a purification and characterization step.

The synthesis of the molecule was carried out in the solid phase, using a Rink Amide-Chemmatrix® resin and a Syro automatic synthesizer (MultiSynTech). The first monomer of the synthesis is manually bound to the resin. Each automatic synthesis cycle is divided into three steps. The first step is deprotection, carried out using a solution of 20% piperidine in DMF (dimethylformammide).

The second step is the coupling reaction between the entering monomer and the growing chain. This reaction is carried out by adding 5 0.22M equivalents (eq) of monomer (FMOC-PNA-G(Bhoc)-OH, FMOC-PNA-A(Bhoc)-OH, FMOC-PNA-C(Bhoc)-OH, FMOC-PNA-T-OH) in NMP (N-methylpirrolidone) and 4.5 0.32M eq of an activator in DMF (in this case HATU) in an alkaline environment with an 8% solution of 2,6-lutidine and DIPEA (N,N-diisopropylethylamine) in DMF. The coupling reaction is repeated, in duplicate, at the point of attachment of the first and second monomer on the preloaded resin, in the passage from the peptide chain to the PNA one, and on the last monomer.

The third step is the “capping” reaction, which serves to block, by acetylation, the sites that have not reacted during the coupling step. The reaction is achieved using a solution containing 6% 2,6-lutidine and 5% acetic anhydride in DMF. Upon completion of the synthesis, the molecules are removed from the solid support.

This reaction is obtained with a solution of TFA (trifluoroacetic acid) and meta-cresol in 4:1 ratios.

The molecule thus obtained is collected by precipitation in diethyl ether.

Once recovered in water, it is purified in HPLC. The column used for purification is a C18 300A 5u Jupiter (® Phenomenex, Inc.). Purification is carried out using a linear gradient from 100% A (water 95%; acetronitrile 5%; 0.1% TFA)-0% B (water 60%; acetonitrile 40%; 0.1% TFA) to 60% A-40% B in 30 minutes. The complete gradient used is 0-5 minutes 0% B; 5-35 minutes 40% B; 35-37 100% B; 37-42 100% B; 42-44 0% B.

Finally, the purified product is analyzed by ESI mass spectroscopy (@ Waters).

Antigene Oligonucleotides for Blocking Gene Transcription.

For the purpose demonstrating that the oligonucleotides of the invention, selected and designed according to the parameters described in the present invention, work to selectively block the transcription of a gene, PNA-based oligonucleotides directed against the MYCN gene were designed and synthesized; they are shown in Table 1.

| SEQ ID NO | PNA SEQUENCE | % GC | mRNA inhibition (%) | Cell prolif. (%) | Phoenix prolif. (%) | NIH-3T3 prolif. (%) |
|---|---|---|---|---|---|---|
| SEQ ID NO: 1 | *ATGCC<u>GGG</u>CATGATCT* | 56.3 | 42 | 70 | 100 | 100 |
| SEQ ID NO: 2 | <u>GGG</u>T<u>GG</u>ATGC<u>GGGGGG</u> | 81.3 | 75 | 32 | 100 | 100 |

-continued

| SEQ ID NO | PNA SEQUENCE | % GC | mRNA inhibition (%) | Cell prolif. (%) | Phoenix prolif. (%) | NIH-3T3 prolif. (%) |
|---|---|---|---|---|---|---|
| SEQ I NO: 3 | GATGCGGGGGGCTCCT | 75 | 68 | 41 | 100 | 100 |
| SEQ ID NO: 4 | GTCGGCGGGAGGTAAG | 68.8 | 65 | 48 | 100 | 100 |
| SEQ ID NO: 5 | GCTGGGTGGATGCGGG | 75 | 62 | 53 | 100 | 100 |
| SEQ ID NO: 6 | TGGACGCGCTGGGTGG | 75 | 60 | 54 | 100 | 100 |
| SEQ ID NO: 7 | CGCGCTGGGTGGATGC | 75 | 58 | 57 | 100 | 100 |
| SEQ ID NO: 8 | GTCTGGACGCGCTGGG | 75 | 54 | 59 | 100 | 100 |
| SEQ ID NO: 9 | CCCTGCAGTCGGCGGG | 81.3 | 51 | 64 | 100 | 100 |
| SEQ ID NO: 10 | CGGCCGCGGGCCGCCA | 93.8 | 51 | 65 | 100 | 100 |
| SEQ ID NO: 11 | GGGAACTGTGTTGGAG | 56.3 | 48 | 68 | 100 | 100 |
| SEQ ID NO: 12 | TGTCTGGACGCGCTGG | 68.8 | 47 | 69 | 100 | 100 |
| SEQ ID NO: 13 | ACGCTCAGGGACCACG | 68.8 | 48 | 66 | 100 | 100 |
| SEQ ID NO: 14 | CCCGGACGAAGATGAC | 62.5 | 40 | 70 | 100 | 100 |
| SEQ ID NO: 15 | ACTGTGTTGGAGCCGA | 56.3 | 37 | 77 | 100 | 100 |
| SEQ ID NO: 16 | CCTGTCGTAGACAGCT | 56.3 | 14 | 90 | 100 | 100 |
| SEQ ID NO: 17 | TGTGACAGTCATCTGT | 56.3 | 10 | 98 | 100 | 100 |
| SEQ ID NO: 18 | GTGACAGTCATCTGTC | 50 | 10 | 98 | 100 | 100 |
| SEQ ID NO: 19 | GACAGTCATCTGTCTG | 50 | 5 | 100 | 100 | 100 |
| SEQ ID NO: 20 | CGTCGATTTCTTCCTC | 50 | 5 | 100 | 100 | 100 |
| SEQ ID NO: 21 | CTCGAGTTTGACTCGC | 56.3 | 1 | 100 | 100 | 100 |
| SEQ ID NO: 22 | GCGCCTCCCCTGATTT | 62.5 | 2 | 100 | 100 | 100 |
| SEQ ID NO: 23 | ATATCCCCCGAGCTTC | 56.3 | 2 | 100 | 100 | 100 |

The PNA oligonucleotides were tested both individually and conjugated with a carrier at the 3' and/or 5' end with the aim of favouring cell membrane permeation. In particular, the oligonucleotides were conjugated to the carboxyl terminus at 3' with the amino acid sequence SEQ ID NO: 43, i.e. proline-lysine-lysine-lysine-arginine-lysine-valine.

The oligonucleotide having SEQ ID NO: 1 is the sequence that was the subject of patent EP 1618195 and represents the control sequence and sequence used for comparison.

The oligonucleotides having SEQ ID NO: 2-15 contain a group of two consecutive guanines (SEQ ID NO: 14, 15), or a group of three consecutive guanines (SEQ ID NO: 13), or two groups of two consecutive guanines (SEQ ID NO: 12), or a group of two guanines and a group of three consecutive guanines (SEQ ID NO: 11, 10, 9, 8 and 7), or two groups of two consecutive guanines and a group of three consecutive guanines (SEQ ID NO: 6 and 4), or a group of two consecutive guanines and two groups of three consecutive guanines (SEQ ID NO: 5), or a group of six consecutive guanines (SEQ ID NO: 3), or a group of six consecutive guanines, a group of three consecutive guanines and a group of two consecutive guanines (SEQ ID NO: 2).

The groups of consecutive guanines are shown underlined in Table 1.

The oligonucleotides having SEQ ID NO: 16-23 do not have groups of consecutive guanines, being negative controls.

Moreover, for the purpose of selectively modulating the transcription of a gene, oligonucleotides having SEQ ID NO: 24-25 were also designed and synthesized; these are shown in Table 2.

TABLE 2

| | | |
|---|---|---|
| SEQ ID NO: 24 | DNA-LNA 25-1 | ATGCCGGGCATGATCT |
| SEQ ID NO: 25 | DNA-LNA 25-2 | ATGCCGGGCATGATCT |

In particular, single-stranded chimeric oligonucleotides, comprising DNA monomers and LNA monomers (SEQ ID NO: 24 and 25) were designed and synthesized.

The DNA bases in the oligonucleotide sequence are shown as bases in boldface type, whereas the LNA monomers are underlined. Each chimeric oligonucleotide molecule was designed and synthesized by inserting the LNA monomers spaced apart by 1, 2 or 3 DNA bases in order to avoid rapid degradation by the endogenous nucleases, as has been reported in the literature (Koch T, Biochem J 2001, 354 (Pt 3):481-4; Koji Nagahama, Bioorg Med Chem Lett, 2009, 19(10):2707-9).

Antisense Oligonucleotides for Blocking Gene Translation.

For the purpose demonstrating that the oligonucleotides of the invention, selected and designed according to the parameters described in the present invention, work to selectively block the translation of the target gene, antisense oligonucleotides having SEQ ID NO: 26-36, directed against the MYCN gene, were designed, synthesized and experimentally analyzed in vitro. They are shown in Table 3.

TABLE 3

| SEQ ID NO | | SENSE SEQUENCE | | ANTISENSE SEQUENCE |
|---|---|---|---|---|
| SEQ ID NO: 26 | siMYCN (795) | UGAAGAUGAUGAAGAGGAA | SEQ ID NO: 57 | UUCCUCUUCAUCAUCUUCA |
| SEQ ID NO: 27 | siMYCN (799) | GAUGAUGAAGAGGAAGAUG | SEQ ID NO: 58 | CAUCUUCCUCUUCAUCAUC |
| SEQ ID NO: 28 | siMYCN (801) | UGAUGAAGAGGAAGAUGAA | SEQ ID NO: 59 | UUCAUCUUCCUCUUCAUCA |
| SEQ ID NO: 29 | siMYCN (808) | GAGGAAGAUGAAGAGGAAG | SEQ ID NO: 60 | CUUCCUCUUCAUCUUCCUC |
| SEQ ID NO: 30 | siMYCN (810) | GGAAGAUGAAGAGGAAGAA | SEQ ID NO: 61 | UUCUUCCUCUUCAUCUUCC |
| SEQ ID NO: 31 | MYCN-PTO (1) as | | | CGTGGAGCAGCTCGGCAT |
| SEQ ID NO: 32 | MYCN-PTO (763) as | | | CAGGGTGTCCTCTCCGGA |
| SEQ ID NO: 33 | siRNA-2'-OMe-RNA 808 | GAGGAAGAUGAAGAGGAAGTT | SEQ ID NO: 62 | CUUCCUCUUCAUCUUCCUCTT |
| SEQ ID NO: 34 | siRNA-2'F-RNA 808 | CAGGAAGAUGAAGAGGAAGUU | SEQ ID NO: 63 | GUUCCUCUUCAUCUUCCUCUU |
| SEQ ID NO: 35 | siRNA-LNA 808 | GAGGAAGAUGAAGAGGAAGTT | SEQ ID NO: 64 | CUUCCUCUUCAUCUUCCUCTT |
| SEQ ID NO: 36 | siRNA-ANA 808 | CAGGAAGAUGAAGAGGAAGAA | SEQ ID NO: 65 | GUUCCUCUUCAUCUUCCUCAA |

Complementary double-stranded oligonucleotides based on RNA (small interfering RNA (siRNA) (SEQ ID NO: 26-30) were produced to selectively modulate the translation of the target gene, MYCN.

Moreover, oligonucleotides based on DNA SEQ ID NO: 31 and 32, in which the phosphodiester bond was modified into phosphorothioate, were produced.

Double-stranded chimeric oligonucleotides: based on RNA monomers and monomers 2'O-Methyl (SEQ ID NO: 33); based on RNA monomers and 2'-Fluoro monomers (SEQ ID NO: 34); based on RNA monomers and LNA monomers (SEQ ID NO: 35) and based on RNA monomers and arabinoside RNA monomers (SEQ ID NO: 36), were also produced. In the oligonucleotide sequences SEQ ID NO: 33-36, the 2'O-Methyl, 2'-Fluoro, LNA and arabinoside (ANA) monomers are shown in boldface, whereas each group of at least two consecutive guanines is underlined.

As the siRNA of the oligonucleotides is double-stranded, the chimera was designed and synthesized in such a manner as to leave two 2'O-Me monomers, or two 2'-Fluoro monomers, or two LNA monomers, or two RNA arabinoside monomers, both in 3' and in 5', unpaired to the complementary strand and thereby avoid rapid degradation by the cell enzymes.

Treatments with Oligonucleotides—QT-PCR

For the purpose of assessing the ability of the oligonucleotides of the present invention to modulate the expression of the target genes, their ability to reduce the quantity of messenger RNA was analyzed using the Real-Time PCR technique.

For this purpose, use was made of 24-well plates, which were seeded with 5.0×104 cells with 0.3 ml of OPTI-MEM (GIBCO BRL) medium, 4% FBS and 2 mM L-glutammine (experiments in triplicate) per well.

The cells were incubated for 24 hours at 37° C., in an atmosphere containing 5% $CO_2$ to permit adherence to the base of the wells.

Each oligonucleotide analyzed, except for the PNA oligonucleotides, was incubated beforehand with 2 μl of Lipofectamine 2000 (Invitrogen), with 0.3 mL of serum-free OPTI-MEM (GIBCO BRL) medium.

For each well, the oligonucleotides were analyzed at the following final concentrations:

- the antisense oligonucleotides siRNA and siRNA gapmer (i.e. the oligonucleotides containing one or more monomers of chemically modified nucleic acids at the 3' or 5' end, while in the central portion they have monomers of nucleic acids that have not been modified or have been modified at the level of the phosphodiester bond as a phosphorothioate bond) were used at 200 nM;
- the antisense oligonucleotides containing phosphorothioate DNA monomers, the RNA antigene oligonucleotides (agRNA) and the oligonucleotides containing DNA monomers and LNA monomers were used at 10 μM;
- the morpholino oligonucleotides were used at a concentration of 1 μM, and
- the PNA oligonucleotides were administered at a concentration of 1 μM.

The cells were treated with the oligonucleotides, adding FBS up to 4% 6 hours after administration of the same. After 24 hours the total RNA was extracted from each well and purified using the RNeasy Mini Kit (QIAGEN).

Assays were performed on 8 cell lines obtained from 5 different human tumours which are correlated with MYCN expression, i.e.:

- as a neuroblastoma model use was made of the cell lines Kelly, IMR-32 (where the MYCN gene is amplified and superexpressed) and SKNBE2c and LAN1 (where the MYCN gene is amplified and superexpressed and the p53 gene is mutated);
- as a rabdomiosarcoma model use was made of the cell line RH30, where the MYCN gene is amplified and superexpressed;
- as a Wilms' tumour model use was made of the cell line WiT49, where the MYCN gene is amplified and superexpressed;
- as a retinoblastoma model use was made of the cell line Y79, where the MYCN gene is amplified and superexpressed; and
- as a model of small cell lung cancer use was made of the cell line H69 where the MYCN gene is amplified and superexpressed.

As a control, use was made of the same cell lines as listed above treated with sterile water instead of oligonucleotides. Each RNA sample was quantified (in duplicate) using a NanoDrop ND-1000 spectrophotometer (NanoDrop Technologies). The first strand of cDNA was produced using the cDNA Synthesis Kit for RT-PCR (Roche). For the cDNA synthesis reaction a total of 1 μg of RNA was used. For the real-time PCR, 10 ng of cDNA in a final volume of 20 μl was used with SYBR Green Master Mix 2× (Applied Biosystems) (3 identical experiments were conducted in triplicate). The sequences and the concentrations of the primer used to carry out the Real-Time PCRs are shown in Table 4. Two housekeeping genes were used as positive controls: GAPDH and beta-actin (ACTB).

The conditions of the QT-PCR reaction were: 10 min at 95° C., 20 sec at 95° C., and 30 sec at 60° C., for 50 cycles.

TABLE 4

| Primer | Sequence | Concentration | SEQ ID NO |
|---|---|---|---|
| MYCN sense | CGACCACAAGGCCCTCAGT | 300 nM | SEQ ID NO: 37 |
| MYCN anti-sense | TGACCACGTCGATTTCTTCCT | 300 nM | SEQ ID NO: 38 |
| ACTB sense | GAGCACAGAGCCTCGCCTTTG | 300 nM | SEQ ID NO: 39 |
| ACTB anti-sense | ACCATCACGCCCTGGTGCCTG | 300 nM | SEQ ID NO: 40 |
| GAPDH sense | CCAATATGATTCCACCCATGGC | 300 nM | SEQ ID NO: 41 |
| GAPDH anti-sense | CTTGATTTTGGAGGGATCTCGC | 300 nM | SEQ ID NO: 42 |

Treatments with Oligonucleotides—Cellular Proliferation Assay.

For the purpose of assessing the gene modulation ability of the oligonucleotides of the present invention, the effect of their administration on cell viability was determined.

For this purpose $5\times10^3$ cells per well were seeded into 96-well cell culture plates (experiments conducted in triplicate) with 100 μl of OPTI-MEM (GIBCO BRL) medium containing 4% FBS and 2 mM of L-glutammine.

The PNA oligonucleotides were administered at different concentrations (1 μM-2.5 μM-5 μM-10 μM) in order to observe a dose-effect relationship.

As regards all the other oligonucleotides, the concentrations at which they administered are listed in the paragraph: Treatments with Oligonucleotides—QT-PCR.

The viability of the treated cells was determined at 48, 72, 96 and 168 hours after treatment.

Cell viability was assessed by means of an ATP-Lite assay (Luminescence ATP Detection Assay System, PerkinElmer) and is reported as the ratio between the average signal of the treated wells compared to the average value of the wells of untreated control cells. The cells were processed following the instructions provided with the kit.

The assays were performed on the same cell lines used to determine the levels of the MYCN gene messenger and listed in the paragraph: Treatments with Oligonucleotides—QT-PCR.

Results

As far as the PNA oligonucleotides are concerned, the results regarding their ability to inhibit the transcription of the MYCN gene and proliferation of Kelly cells are shown in Table 1. Table 6 shows the values (in percentage form) of the proliferating Kelly cells at the different concentrations of PNA analyzed.

In particular, the results shown in Table 1 and in Table 5 demonstrate that the sequences SEQ ID NO: 2-SEQ ID NO: 13 have greater antigene effectiveness than the sequence SEQ ID NO: 1, the subject of patent EP 1618195.

Sequences SEQ ID NO: 7-SEQ ID NO: 12 (containing two groups of two or three consecutive Gs) show greater antigene effectiveness than the sequences SEQ ID NO: 1, and SEQ ID NO: 13-SEQ ID NO: 15 (containing only one group of two or three consecutive Gs).

Sequences SEQ ID NO: 4-SEQ ID NO: 6 (containing three groups of two or three consecutive Gs) show greater antigene effectiveness than the sequences SEQ ID NO: 7-SEQ ID NO: 12 (containing two groups of two or three consecutive Gs).

SEQ ID NO: 3, containing a group of six consecutive Gs, shows greater antigene effectiveness than the sequences SEQ ID NO: 1 and sequences SEQ ID NO: 4-SEQ ID NO: 12 containing one or two or three groups of Gs (in which each group consists of at most two or three consecutive Gs).

Sequence SEQ ID NO: 2, containing three groups of consecutive Gs, which, in addition to two groups of two and three consecutive Gs, also comprises a group of six consecutive Gs, shows greater antigene effectiveness than both SEQ ID NO: 3, containing only one group of six Gs, and sequences SEQ ID NO: 1 and sequences SEQ ID NO: 4-SEQ ID NO: 12 containing one or two or three groups of Gs (in which each group consists of at most two or three consecutive Gs).

TABLE 5

| SEQ ID NO | Sequence | Cell Prolif (%) 1 μM 72 h | Cell Prolif (%) 2,5 μM 72 h | Cell Prolif. (%) 5 μM 72 h | Cell Prolif. (%) 10 μM 72 h |
|---|---|---|---|---|---|
| SEQ ID NO: 1 | *ATGCCGGGCATGATCT* | 89 | 66 | 50 | 24 |
| SEQ ID NO: 2 | GGGTGGATGCGGGGGG | 74 | 32 | 12 | 2 |
| SEQ ID NO: 3 | GATGCGGGGGGCTCCT | 78 | 41 | 19 | 3 |
| SEQ ID NO: 4 | GTCGGCGGGAGGTAAG | 78 | 48 | 21 | 3 |
| SEQ ID NO: 5 | GCTGGGTGGATGCGGG | 79 | 53 | 27 | 5 |
| SEQ ID NO: 6 | TGGACGCGCTGGGTGG | 82 | 59 | 35 | 13 |
| SEQ ID NO: 7 | CGCGCTGGGTGGATGC | 80 | 54 | 31 | 8 |
| SEQ ID NO: 8 | GTCTGGACGCGCTGGG | 80 | 57 | 32 | 11 |
| SEQ ID NO: 9 | CCCTGCAGTCGGCGGG | 86 | 64 | 42 | 20 |
| SEQ ID NO: 12 | TGTCTGGACGCGCTGG | 84 | 60 | 40 | 16 |

The results demonstrate that the inhibition effect of these PNAs on the translated protein of the target genes is highly selective and specific. Moreover, it was observed that the arrest of growth of the tumour cells used as a model (characterized by amplification of the MYCN gene) was directly followed by apoptosis following the administration of the antigene PNAs.

In general, the PNA antigene oligonucleotides having SEQ ID: 2-SEQ ID NO: 13 (containing one or more groups of Gs) have greater antigene effectiveness (i.e. inhibition of MYCN mRNA and of the proliferation of tumour cells with MYCN expression) compared to PNA oligonucleotides devoid of groups of Gs (SEQ ID NO: 16-SEQ ID NO: 23).

Moreover, the oligonucleotides having SEQ ID NO 1-23 were administered in lines of fibroblastoid-type cells (NIH-3T3 and Phoenix) and the results are shown in Table 1 (last two columns).

The results clearly demonstrate that the oligonucleotides analyzed are not specifically effective against and are not toxic for these cells (i.e. cells that do not express the target gene, which in this case is MYCN).

In fact, no changes were observed in cellular proliferation in these two lines of non-tumoural fibroblasts, and this result means that the PNA oligonucleotides act with a specific effect of inhibiting the expression of MYCN, whereas they do not have a non-specific, toxic effect in cells that do not express MYCN.

Therefore, it may be deduced that the PNA oligonucleotides designed on the basis of the parameters described in the present invention act specifically and effectively on the target gene and therefore on the cells which express/overexpress this gene.

The PNAs having SEQ ID NO: 1-12 were also tested on different cell lines which overexpress MYCN (Kelly, SKNBE2c, RH30, WiT49, WERI-Rb1 1 and H69). The results are shown in Table 6 and confirm the selectivity and specificity of the inhibition effect of the PNAs on the product of protein translation of the MYCN gene.

TABLE 6

| SEQ ID NO | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 | SEQ ID NO: 9 | SEQ ID NO: 10 | SEQ ID NO: 11 | SEQ ID NO: 12 |
|---|---|---|---|---|---|---|---|---|---|---|---|---|
| Kelly % mRNA | 48 | 75 | 68 | 65 | 62 | 60 | 58 | 54 | 51 | 51 | 50 | 50 |
| Kelly % cell prol. | 66 | 32 | 41 | 48 | 53 | 54 | 57 | 59 | 60 | 64 | 64 | 65 |
| SKNBE2c % mRNA | 41 | 75 | 68 | 60 | 59 | 62 | 60 | 62 | 58 | 41 | 40 | 40 |
| SKNBE2c % cell prol. | 72 | 52 | 53 | 59 | 64 | 57 | 58 | 56 | 64 | 70 | 71 | 71 |
| RH30 % mRNA | 39 | 74 | 65 | 57 | 56 | 56 | 55 | 58 | 50 | 29 | 31 | 32 |
| RH30 % cell prol. | 76 | 56 | 59 | 62 | 64 | 64 | 63 | 60 | 71 | 80 | 78 | 77 |
| WiT49 % mRNA | 62 | 78 | 75 | 73 | 69 | 68 | 70 | 72 | 66 | 60 | 60 | 62 |
| WiT49 % cell prol. | 74 | 54 | 57 | 60 | 63 | 65 | 60 | 62 | 68 | 70 | 72 | 73 |
| WERI-Rb1 % mRNA | 31 | 46 | 43 | 41 | 38 | 37 | 38 | 40 | 36 | 30 | 30 | 30 |
| WERI-Rb1 % cell prol. | 82 | 79 | 78 | 79 | 80 | 80 | 79 | 78 | 79 | 85 | 84 | 84 |
| H69 % mRNA | 40 | 58 | 55 | 55 | 54 | 55 | 55 | 56 | 50 | 41 | 41 | 40 |
| H69 % cell prol. | 77 | 61 | 63 | 66 | 68 | 69 | 67 | 66 | 70 | 79 | 78 | 78 |

The antigene PNA oligonucleotide having SEQ ID NO: 5 was analyzed in a more detailed manner.

In particular, modified oligonucleotides, in which the groups of consecutive guanines present in the sequence were modified (the groups of consecutive guanines are underlined, whereas the modified nucleotides are in boldface type) so as to interrupt the consecutiveness of the guanines, were synthesized and analyzed in vitro on Kelly cells (which overexpress MYCN).

The results (summarized in Table 7) clearly demonstrate that the fact of the guanines being consecutive is of fundamental importance for the purposes of the activity of modulating the gene's expression. In fact, the PNAs having SEQ ID NO: 43, in which all the groups of consecutives guanine of the PNAs having SEQ ID NO: 5 were mutated, causes the inhibitory activity of the PNAs to be lost, whereas the mutation of one or two of the three groups of consecutive guanines considerably compromises, but does not completely suppress, the inhibitory activity of the molecule.

TABLE 7

| SEQ ID NO | SEQUENCE | mRNA Inhibition (%) (Kelly) | (Kelly) Cell Prolif. % |
|---|---|---|---|
| SEQ ID NO: 5 | GCTGGGTGGATGCGGG | 62 | 53 |
| SEQ ID NO: 43 | GCTGAGTCGATGCGTG | 0 | 100 |
| SEQ ID NO: 44 | GCTGAGTGGATGCGTG | 25 | 89 |
| SEQ ID NO: 45 | GCTGGGTCGATGCGGG | 47 | 69 |
| SEQ ID NO: 46 | GTTGGGTGGATGTGGG | 58 | 60 |

Chimeric oligonucleotides comprising DNA monomers and LNA monomers and having the MYCN gene as their target were tested in vitro on alveolar rabdomyosarcoma cells (RH30). The results are summarized in Table 8 and demonstrate these oligonucleotides have an intense, specific antigene activity.

TABLE 8

| SEQ ID NO | NAME | SEQUENCE | mRNA Inhibition (%) | Cell Prolif. (%) |
|---|---|---|---|---|
| SEQ ID NO: 24 | DNA-LNA 25-1 | ATGCCGGGCATGA TCT | 23 | 75 |
| SEQ ID NO: 25 | DNA-LNA 25-2 | ATGCCGGGCATGA TCT | 24 | 78 |

The antisense oligonucleotides designed and synthesized by the Applicant according to the parameters described in the present invention were analyzed in vitro on rabdomyosarcoma cells (RH30). The results are summarized in the Table 9 and show that the oligonucleotides are capable of inhibiting the MYCN transcript in a specific and effective manner; moreover, they are also capable of selectively inhibiting tumour cell proliferation in a more effective manner than the standard antisense oligonucleotides presently available for the MYCN gene (Chung D H, Bioch Bioph Res Commun, 2006, 351(1):192-7.

In particular, the siRNA identified by the Applicant and directed against MYCN mRNA, described in Table 11, exert an antisense activity with an inhibition of MYCN mRNA ranging from a minimum of 70% to a maximum of 85%.

TABLE 9

| SEQ ID NO | | SEQUENCE SENSE | SEQUENCE ANTISENSE | mRNA Inhibition (%) | Cell Prolif. (%) |
|---|---|---|---|---|---|
| SEQ ID NO: 26 | siMYCN (795) | UGAAGAUGAU GAAGAGGAA | UUCCUCUUCA UCAUCUUCA | 82 | 28 |
| SEQ ID NO: 27 | siMYCN (799) | GAUGAUGAAG AGGAAGAUG | CAUCUUCCUC UUCAUCAUC | 70 | 43 |
| SEQ ID NO: 28 | siMYCN (801) | UGAUGAAGAG GAAGAUGAA | UUCAUCUUCC UCUUCAUCA | 78 | 35 |
| SEQ ID NO: 29 | siMYCN (808) | GAGGAAGAUG AAGAGGAAG | CUUCCUCUUC AUCUUCCUC | 85 | 28 |
| SEQ ID NO: 30 | siMYCN (810) | GGAAGAUGAA GAGGAAGAA | UUCUUCCUCU UCAUCUUCC | 81 | 30 |
| SEQ ID NO: 31 | MYCN-PTO (1) as | | CGTGGAGCAG CTCGGCAT | 34 | 73 |
| SEQ ID NO: 32 | MYCN-PTO (763) as | | CAGGGTGTCC TCTCCGGA | 45 | 65 |
| SEQ ID NO: 33 | siRNA-2'-OMe-RNA 808 | GAGGAAGAUG AAGAGGAAGT T | CUUCCUCUUC AUCUUCCUCT T | 13 | 85 |
| SEQ ID NO: 34 | siRNA-2'F-RNA 808 | CAGGAAGAUG AAGAGGAAGU U | GUUCCUCUUC AUCUUCCUCU U | 59 | 52 |
| SEQ ID NO: 35 | siRNA-LNA 808 | GAGGAAGAUG AAGAGGAAGT T | CUUCCUCUUC AUCUUCCUCT T | 34 | 68 |
| SEQ ID NO: 36 | siRNA-ANA 808 | CAGGAAGAUG AAGAGGAAGA A | GUUCCUCUUC AUCUUCCUCA A | 69 | 35 |

For the purpose of verifying whether the oligonucleotides of the present invention are capable of lowering the concentrations of the chemotherapeutic agents presently used in the therapeutic protocols against cancer, the same were administered in concomitance with chemotherapy drugs.

Studies were conducted on the effect of associations between PNA and chemotherapy drugs (carboplatin, etoposide (VP16), cisplatin and vincristine) on different human and mouse neuroblastoma tumour cell lines (SMS-KAN, LAN 1, IMR-32, SMS-KCN, Kelly, NHO2A, SKNBE2c).

The therapeutic schedule used in the treatments carried out provided for the cells to be treated with PNA and then afterwards, at a pre-established time (it could be 6 or 12 hours) the chemotherapeutic agent was administered.

The results demonstrate that the association of these compounds with the oligonucleotides of the invention determines, at specific concentration ranges, a greater therapeutic effect than individual treatments with the same compounds.

In particular, it may be observed that the treatment—be it concomitant and simultaneous or at different time intervals (3 hours, 6 hours, 12 hours, 24 hours, 48 hours, 72 hours, etc.)—with a combination consisting of the oligonucleotides of the invention and other compounds with a pharmacological effect serves to enhance the desired therapeutic effect. Therefore, combining one or more of the oligonucleotides identified by the Applicant with chemotherapy drugs makes it possible to reduce the chemotherapy drug concentration by as much as 10 times compared to the present standard therapeutic concentration while still obtaining the same effect.

In particular, the results of this study demonstrate that SEQ ID NO: 1 has a synergic effect, in terms of inhibiting cell proliferation, when it is administered in combination with vincristine, or etoposide, or carboplatin, or cisplatin, compared to the effects obtained in treatments with the oligonucleotide or with the aforesaid chemotherapeutic agents on their own.

EXAMPLE 2

For the purpose of supporting the present invention, the oligonucleotides summarized in Table 10 were also synthesized. In particular, Table 10 shows the oligonucleotide sequences, the SEQ ID NO, the percentage value of the (G+C) content and the gene the synthesized oligonucleotides are directed against. The synthesis of the oligonucleotides was achieved as in example 1.

TABLE 10

| | SEQ ID NO | | % GC |
|---|---|---|---|
| MYCN | SEQ ID NO: 66 | TCGGGAGCAGTGGGCA | 68.8 |
| | SEQ ID NO: 67 | GCGGGTCGCGGGCACG | 87.5 |
| | SEQ ID NO: 68 | TGGAGGTCGGCGCCGG | 81.3 |
| | SEQ ID NO: 69 | TCGGCGGGAGGTAAGG | 68.8 |
| MYC | SEQ ID NO: 70 | CTCAGAGGCTTGGCGG | 68.8 |
| | SEQ ID NO: 71 | GCGGCCGGCTAGGGTG | 81.3 |
| | SEQ ID NO: 72 | CGGCCGGCTAGGGTGG | 81.3 |
| | SEQ ID NO: 73 | CGACGGCGGTGGCGGG | 87.5 |
| | SEQ ID NO: 74 | GGACGGGGGCGGTGGA | 81.3 |
| BIRC5 | SEQ ID NO: 75 | GCGGCGGCATGGGTGC | 81.3 |
| | SEQ ID NO: 76 | GGCGGCGGCATGGGTG | 81.3 |
| ALK | SEQ ID NO: 77 | GCAGGAGAGGACGGTA | 62.5 |
| | SEQ ID NO: 78 | CAGGAGAGGACGGTAC | 62.5 |
| | SEQ ID NO: 79 | GGCAGGAGAGGACGGT | 68.8 |
| BCL2 | SEQ ID NO: 80 | GGATGGCGCACGCTGG | 75.0 |
| | SEQ ID NO: 81 | GGGAAGGATGGCGCAC | 68.8 |
| | SEQ ID NO: 82 | CCACGGTGGTGGAGGA | 68.8 |
| PLK4 | SEQ ID NO: 83 | ACGGCAAGCGGCGGGA | 75.0 |
| | SEQ ID NO: 84 | GGACGGCAAGCGGCGG | 81.3 |

The following, in particular, were synthesized: SEQ ID NO: 66-69 directed against MYCN, SEQ ID NO: 70-74 directed against MYC, SEQ ID NO: 75, 76 directed against BIRC5, SEQ ID NO: 77-79 directed against ALK, SEQ ID NO: 80-82 directed against BCL2 and SEQ ID NO: 83, 84 directed against PLK4.

The oligonucleotides were tested in vitro (at a concentration of 2.5 μM) to determine their ability to inhibit the transcription of the gene they are directed against by measuring the levels of the gene messenger in cellular models in which the gene of interest is overexpressed. The methods used are the ones described in example 1.

In particular, SEQ ID NO: 66-69 (directed against MYCN) were tested in vitro in the Kelly and H69 cell lines; SEQ ID NO: 70-74 (directed against MYC) were tested in vitro in the H82 and RD cell lines, SEQ ID NO: 75, 76 (directed against BIRC5) were tested in vitro in the Kelly cell line, SEQ ID NO: 77-79 (directed against ALK) were tested in vitro in the Kelly cell line, SEQ ID NO: 80-82 (directed against BCL2) were tested in vitro in the Kelly cell line and SEQ ID NO: 83, 84 (directed against PLK4) were tested in vitro in the Kelly cell line.

The ability of the tested oligonucleotides to inhibit the messenger of the gene of interest was measured and the proliferative capacity of the cells following administration of the oligonucleotides was also assessed. The results are summarized in Table 11.

The data show a potent inhibitory activity against the mRNA of the target gene and an inhibition of cell proliferation which rises with increases in the number of groups of Gs present in the sequence of the oligonucleotide.

TABLE 11

| | SEQ ID NO | | mRNA inhibit. (%) | Cell Prolif. (%) |
|---|---|---|---|---|
| MYCN Kelly | SEQ ID NO: 66 | TCGGGAGCACTGGGCA | 57 | 60 |
| | SEQ ID NO: 67 | GCGGGTCGCGGGCACG | 60 | 56 |
| | SEQ ID NO: 68 | TGGAGGTCGGCCCCGG | 74 | 35 |
| | SEQ ID NO: 69 | TCGGCGGGAGGTAAGG | 76 | 30 |

TABLE 11-continued

| | SEQ ID NO | | mRNA inhibit. (%) | Cell Prolif. (%) |
|---|---|---|---|---|
| MYCN H69 | SEQ ID NO: 66 | TCGGGAGCAGTGGGCA | 41 | 73 |
| | SEQ ID NO: 67 | GCGGGTCGCGGGCACG | 42 | 71 |
| | SEQ ID NO: 68 | TGGAGGTCGGCGCCGG | 62 | 49 |
| | SEQ ID NO: 69 | TCGGCGGGAGGTAAGG | 67 | 45 |
| MYC H82 | SEQ ID NO: 70 | CTCAGAGGCTTGGCGG | 43 | 79 |
| | SEQ ID NO: 71 | GCGGCCGGCTAGGGTG | 46 | 75 |
| | SEQ ID NO: 72 | CGGCCGGCTAGGGTGG | 52 | 64 |
| | SEO ID NO: 73 | CGACGGCGGTGGCGGG | 56 | 65 |
| | SEQ ID NO: 74 | GGACGGGGGCGGTGGA | 61 | 61 |
| MYC RD | SEQ ID NO: 70 | CTCAGAGGCTTGGCGG | 34 | 73 |
| | SEQ ID NO: 71 | GCGGCCGGCTAGGGTG | 42 | 65 |
| | SEQ ID NO: 72 | CGGCCGGCTAGGGTGG | 58 | 53 |
| | SEQ ID NO: 73 | CGACGGCGGTGGCGGG | 59 | 51 |
| | SEQ ID NO: 74 | GGACGGGGGCGGTGGA | 64 | 47 |
| BIRC5 Kelly | SEQ ID NO: 75 | GCGGCGGCATGGGTGC | 69 | 43 |
| | SEQ ID NO: 76 | GGCGGCGGCATGGGTG | 78 | 35 |
| ALK Kelly | SEQ ID NO: 77 | GCAGGAGAGGACGGTA | 57 | 55 |
| | SEQ ID NO: 78 | CAGGAGAGGACGGTAC | 68 | 46 |
| | SEQ ID NO: 79 | GGCAGGAGAGGACGGT | 79 | 39 |
| BCL2 Kelly | SEQ ID NO: 80 | GGATGGCGCACGCTGG | 59 | 62 |
| | SEQ ID NO: 81 | GGGAAGGATGGCGCAC | 62 | 58 |
| | SEQ ID NO: 82 | CCACGGTGGTGGAGGA | 68 | 55 |
| PLKA4 Kelly | SEQ ID NO: 83 | ACGGCAAGCGGCGGGA | 62 | 59 |
| | SEQ ID NO: 84 | GGACGGCAAGCGGCGG | 74 | 49 |

Finally, the oligonucleotides having SEQ ID NO 66-84 were administered in cell lines of a fibroblastoid type (Phoenix and NIH-3T3). In these cells the oligonucleotides tested did not show to be toxic.

These results indicate that the PNA oligonucleotides act through a specific inhibition effect on the expression of the gene of interest, whereas they do not have any non-specific, toxic effect in cells which do not express the gene.

It can thus be deduced that the PNA oligonucleotides designed on the basis of the parameters described in the present invention act specifically and effectively on the target gene and therefore on the cells which express/over-express this gene.

The invention claimed is:

1. A method of treating a tumor in a patient in need thereof with a composition comprising at least one single strand anti-gene oligonucleotide complementary to the anti-sense DNA strand of a target gene said target gene being selected from MYCN and MYC, said oligonucleotide comprising 6-30 nucleotides, and comprising a sequence comprising at least three groups of at least two consecutive guanines, said tumor being caused by an overexpression of said target gene, said method comprising administering to said patient in need an effective amount of said composition;

inhibiting said target gene expression; and treating said patient.

2. The method according to claim 1, wherein said composition is in combination with a compound with pharmacological action selected from the group consisting of: NGF, somatostatin, retinoic acid, actinomycin D, asparaginase, bleomycin, busulphan capecitabine, carboplatin, cyclophosphamide, cyclosporine, cisplatin, cytarabine, clorambucil, dacarbazine, daunorubicin, docetaxel, doxorubicin hydrochloride, epirubicin hydrochloride, etoposide, fludarabine phosphate, fluorouracil, gemcitabine, idarubicin hydrochloride, hydroxyurea, ifophosphamide, irinotecan hydrochloride, melphalan, mercaptopurine, methotrexate, mitomycin, mitoxantrone, oxaliplatin, paclitaxel, procarbazine, raltitrexed, streptozocin, tegafururacil, temozolomide, thioguanine, thiotepe, topotecan, vinblastine, vincristine sulphate, vindesine and vinorelbine.

3. The method according to claim 1, wherein said tumor is an adult or pediatric tumor selected from the group consisting of: neuroblastoma, retinoblastoma, medulloblastoma, ependymoma, pheochromocytoma, embryonal carcinoma, germ cell tumour, alveolar rabdomyosarcoma, embryonal rabdomiosarcoma, Wilms tumor, clear cell sarcoma of the kidney, synovial sarcoma, hepatoblastoma, acute lymphoid leukaemia, chronic lymphoid leukaemia, acute lymphoblastic leukaemia, chronic lymphoblastic leukaemia, Burkitt's lymphoma, acute myeloid leukaemia, chronic myeloid leukaemia, acute megakaryoblastic leukaemia, B chronic lymphoid leukaemia, T-cell leukaemia, lymphomas, small cell lung cancer (microcytoma), lung adenocarcinoma, squamous cell lung carcinoma, typical and atypical primary lung cancer, large cell lung carcinoma, large-cell neuroendocrine lung carcinoma, glioblastoma, hepatocarcinoma, basal cell carcinoma, ovarian tumour, breast tumor and colon cancer.

4. The method according to claim 1, wherein the groups of at least two consecutive guanines are continuous with each other.

5. The method according to claim 1, wherein the groups of at least two consecutive guanines are spaced apart by at least one nucleotide, said nucleotide not being a guanine.

6. The method according to claim 1, wherein the groups of at least two consecutive guanines are at least four, five or six in number.

7. The method according to claim 1, wherein said oligonucleotide is conjugated with a carrier sequence at the 3' and/or 5' end of said oligonucleotide, said carrier being selected from the group consisting of: SEQ ID NO: 47-56.

8. The method according to claim 1, wherein said oligonucleotide is at least one molecule of natural nucleic acid, at least one molecule of natural nucleic acid chemically modified, or at least one molecule of synthetic nucleic acid selected from PNA, LNA or morpholino, at least one molecule of synthetic nucleic acid chemically modified or a combination of said natural nucleic acid and said synthetic nucleic acid.

9. The method according to claim 8, wherein said PNA has a modified backbone wherein the alpha carbon has the side chain of arginine or lysine as a substituent.

10. The method according to claim 1, wherein said oligonucleotide is selected among: SEQ ID NO: 2-15, SEQ ID NO: 24, 25.

11. The method according to claim 10, wherein SEQ ID NO: 2-15, 66-69, 24, 25 are directed against the MYCN gene.

12. The method according to claim 10, wherein said oligonucleotide is conjugated at the 5' and/or 3' end with SEQ ID NO: 47.

13. The method according to claim 1, wherein said combination is SEQ ID: NO 1 and carboplatin, or etoposide or cisplatin or vincristine; or SEQ ID: NO 5 and carboplatin, or etoposide or cisplatin or vincristine.

14. The method according to claim 1, wherein the tumor is selected from the group consisting of: neuroblastoma, Wilms' tumor, retinoblastoma and small cell lung cancer.

15. The method according to claim 1, wherein said oligonucleotide is selected from among: SEQ ID NO:70-74 directed against the gene MYC.

* * * * *